United States Patent [19]

Bundy et al.

[11] 4,138,575

[45] Feb. 6, 1979

[54] 11-DEOXY-16-PHENOXY-PGF COMPOUNDS

[75] Inventors: Gordon L. Bundy, Portage; Norman A. Nelson, Galesburg, both of Mich.

[73] Assignee: The Upjohn Company, Kalamazoo, Mich.

[21] Appl. No.: 897,217

[22] Filed: Apr. 17, 1978

Related U.S. Application Data

[62] Division of Ser. No. 609,410, Sep. 2, 1975.

[51] Int. Cl.$^2$ .......................................... C07C 177/00
[52] U.S. Cl. .................................. 560/55; 260/410; 260/410.5; 260/410.9 R; 562/465
[58] Field of Search ............... 560/55; 260/410, 410.5, 260/410.9, 520 R

[56] References Cited

U.S. PATENT DOCUMENTS 3,935,261   1/1976   Caton et al. ........................... 560/55

OTHER PUBLICATIONS

Derwent Abstracts 13443w/08, JA9109-342, 10/17/74.
Derwent Abstract 81238x/44, BE840-924, 10/20/76.

*Primary Examiner*—Paul J. Killos
*Attorney, Agent, or Firm*—Robert A. Armitage

[57] ABSTRACT

11-Deoxy prostaglandin type compounds, i.e. prostaglandin type compounds in which the 11-hydroxy group is replaced by hydrogen, are disclosed, with processes for making them. These compounds are useful for a variety of pharmacological purposes, including anti-ulcer, inhibition of platelet aggregation, increase of nasal patency, and labor induction at term.

4 Claims, No Drawings

11-DEOXY-16-PHENOXY-PGF COMPOUNDS

This is a division of application Ser. No. 609,410, filed Sept. 2, 1975.

BACKGROUND OF THE INVENTION

This invention relates to novel compositions of matter, to novel methods for producing those, and to novel chemical intermediates useful in those processes. Particularly, this invention relates to certain novel analogs of prostaglandin E and prostaglandins $F_\alpha$ and $F_\beta$, in which the 11-hydroxy is replaced by hydrogen, i.e. the ring carbon atom adjacent to the site of attachment of the side chain attached at C-12 bears no hydroxyl substituent.

The known prostaglandins include, for example, prostaglandin $E_1$ (PGE$_1$), prostaglandin $E_2$ (PGE$_2$), prostaglandin $F_1$ alpha and beta (PGF$_{1\alpha}$ and PGF$_{1\beta}$) and prostaglandin $F_2$ alpha and beta (PGF$_{2\alpha}$ and PGF$_{2\beta}$). Each of the above-mentioned known prostaglandins is a derivative of prostanoic acid which has the following structure and atom numbering:

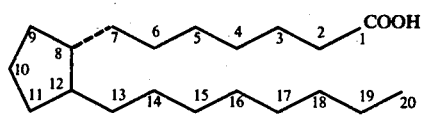

I

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

PGE$_1$ has the following structure:

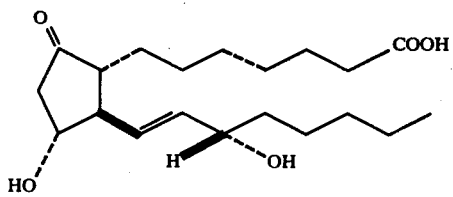

II

PGE$_2$ has the following structure:

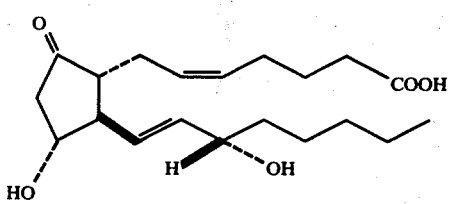

III

PGF$_{1\alpha}$ has the following structure:

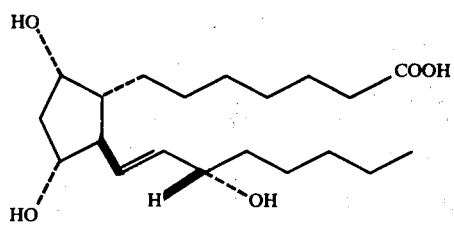

IV

PGF$_{1\beta}$ has the following structure:

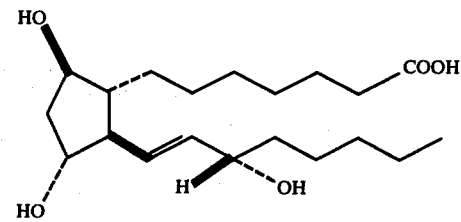

V

PGF$_{2\alpha}$ has the following structure:

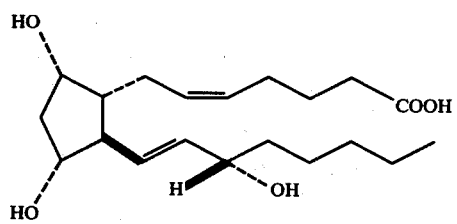

VI

PGF$_{2\beta}$ has the following structure:

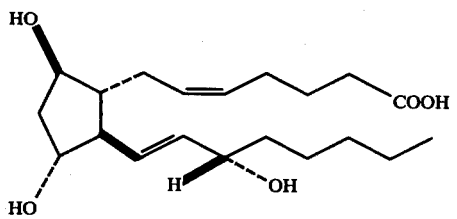

VII

In formulas II to VII, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring. The side-chain hydroxy at C-15 at formulas II to VII is in S configuration. See Nature, 212, 38 (1966) for discussion of the stereochemistry of the prostaglandins.

Molecules of the known prostaglandins each have several centers of asymmetry, and can exist in racemic (optically inactive) form and in either of the two enantiomeric (optically active) forms, i.e. the dextrorotatory and levorotatory forms. As drawn, formulas II to VII each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. The mirror image of each of formulas II to VII represents the other enantiomer of that prostaglandin. The racemic form of a prostaglandin contains equal numbers of both enantiomeric molecules, and one of formulas II to VII and the mirror image of that formula is needed to represent correctly the corresponding racemic prostaglandin. For convenience hereinafter, use of the terms PGE$_1$, PGE$_2$, PGF$_{1\alpha}$, PGF$_{1\beta}$, PGF$_{2\alpha}$, PGF$_{2\beta}$, and the like, will mean the optically active form of that prostaglandin with the same absolute configuration as PGE$_1$ obtained from mammalian tissues. When reference to the racemic form of one of those prostaglandins is intended, the word "racemic" or "dl" will precede the prostaglandin name, thus, "racemic PGE$_2$" or "dl-PGF$_{2\alpha}$".

PGE$_1$, PGE$_2$, PGF$_{1\alpha}$, PGF$_{2\alpha}$, PGF$_{1\beta}$, and PGF$_{2\beta}$ and their esters, acylates and pharmacologically acceptable salts, are extremely potent in causing various biological responses. For that reason, these compounds are useful for pharmacological purposes. See, for example, Bergstrom et al., pharmacol. Rev. 20, 1 (1968) and references cited therein. A few of those biological responses are systemic blood pressure lowering in the case of the PGE and PGF$_\beta$ compounds as measured, for example, in anesthetized (pentobarbital sodium) pentolinium-treated rats with indwelling aortic and right heart cannulas; stimulation of smooth muscle as shown, for example, by tests on strips on guinea pig ileum, rabbit duodenum, or gerbil colon; potentiation of other smooth muscle stimulants; lipolytic activity as shown by antagonism of epinephrine-induced mobilization of free fatty acids or inhibition of the spontaneous release of glycerol from isolated rat fat pads; inhibition of gastric secretion in the case of the PGE compounds as shown in dogs with secretion stimulated by food or histamine infusion; activity on the central nervous system; controlling spasm and facilitating breathing in asthmatic conditions; and decreasing blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits and monkeys.

For example, these compounds and especially the PGE compounds, are useful in mammals, including man, as nasal decongestants. For this purpose, the compounds are used in a dose range of about 10 $\mu$g. to about 10 mg. per ml. of a pharmacologically suitable liquid vehicle or as an aerosol spray, both for topical application.

The PGE, PGF$_\alpha$ and PGF$_\beta$ compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other antiasthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

The PGE compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, PGF$_\alpha$ and PGF$_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF$_\alpha$, and PGF$_\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, PGE compound, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE and PGF$_\beta$ compounds are useful as hypotensive agents to reduce blood pressure in mammals, including man. For this purpose, the compounds are administered by intravenous infusion at the rate about 0.01 to about 50 μg. per kg. of body weight per minute or in single or multiple doses of about 25 to 500 μg. per kg. of body weight total per day.

The PGE, PGF$_\alpha$, and PGF$_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, PGF$_\alpha$, and PGF$_\beta$ compounds are useful in controlling the reproductive cycle in menstruating female mammals. By the term menstruating female mammals is meant animals which are mature enough to menstruate but not so old that regular menstruation has ceased. For this purpose the prostaglandin is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

The PGE and PGF compounds are useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by PGE and PGF compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the PGE and PGF compounds are administered locally or systemically.

PGE$_2$, for example, is administered orally or vaginally at doses of about 5 to 50 mg. per treatment of an adult female human, with from one to five treatments per 24 hour period. PGE$_2$ is also administered intramuscularly or subcutaneously at doses of about one to 25 mg. per treatment. The exact dosages for these purposes depend on the age, weight, and condition of the patient or animal.

As mentioned above, the PGE compounds are potent antagonists of epinephrine-induced mobilization of free fatty acids. For this reason, this compound is useful in experimental medicine for both in virto and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGE, PGF$_\alpha$, and PGF$_\beta$ compounds are also useful in reducing the undesirable gastrointestinal effects resulting from systemic administration of anti-inflammatory prostaglandin synthetase inhibitors, and are used for that purpose by concomitant administration of the prostaglandin and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats in inhibited by concomitant oral administration of certain prostaglandins of the E and A series, including PGE$_1$, PGE$_2$, PGE$_3$, 13,14-dihydro-PGE$_1$, and the corresponding 11-deoxy-PGE compounds. The prostaglandins are useful, for example, in reducing the undesirable gastrointestinal effects resulting from systemic administration of indomethacin, phenylbutazone, and aspirin. These are substances specifically mentioned in Partridge et al. as non-steroidal anti-inflammatory agents. But these are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally, or, alternatively, orally or, in the case of women vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

The $PGF_\alpha$ compounds are useful in the treatment of shock (hemorrhagic shock, endotoxin shock, cardiogenic shock, surgical shock, or toxic shock). Shock is marked by pallor and clamminess of the skin, decreased blood pressure, feeble and rapid pulse, decreased respiration, restlessness, anxiety, and sometimes unconsciousness. Shock usually follows cases of injury and trauma. Expert and fast emergency measures are required to successfully manage such shock conditions. Accordingly, prostaglandins, combined with a pharmaceutical carrier which adapts the prostaglandin for intramuscular, intravenous, or subcutaneous use, are useful, especially in the early stages of shock where increased blood pressure is a critical factor, for aiding and maintaining adequate blood flow, perfusing the vital organs, and exerting a presser response by constricting veins and raising blood pressure to normal levels. Accordingly, the prostaglandins are useful in preventing irreversible shock which is characterized by a profound fall in blood pressure, dilation of veins, and venus blood pooling. In the treatment of shock, the prostaglandin is infused at a dose of 0.1 - 25 mcg./kg./min. The prostaglandin may advantageously be combined with known vasoconstrictors; such as phenoxybenzamine, norepinephrine, norephrine, and the like. Further, when used in the treatment of shock the prostaglandin may be combined with steroids (such as, hydrocortisone or methylprednisolone), tranquilizers, and antibiotics (such as lincomycin or clindamycin).

The PGE, $PGF_\alpha$, and $PGF_\beta$ are useful in domestic animals as an abortifacient (especially for feedlot heifers), as an aid to estrus detection, and for regulation or synchronization of estrus. Domestic animals include horses, cattle, sheep and swine.

The regulation or synchronization of estrus, as well as estrus detection, allows for more efficient management of both conception and labor by enabling a herdsman to breed all his female animals in short predefined intervals. This results in a higher percentage of live births than the percentage achieved by natural control. The prostaglandin is injected or applied in a feed at doses of 0.1-100 mg. per animal per day and may be combined with other agents such as steroids. Dosing schedules will depend on the species treated. For example, mares are given prostaglandin 5-8 days after ovulation and return to estrus. Cattle, are treated at regular intervals over a 3 week period to advantageously bring all into estrus at the same time.

SUMMARY OF THE INVENTION

It is a purpose of this invention to provide novel 11-deoxy-prostaglandin analogs. It is a further purpose to provide esters, lower alkanoates, and pharmacologically acceptable salts of said analogs. It is a further purpose to provide novel processes for preparing said analogs and esters. It is still a further purpose to provide novel intermediates useful in said processes.

The presently described acids and esters of the 11-deoxy-prostaglandin analogs include compounds of the following formula, and also the racemic compounds of that formula and the mirror image thereof:

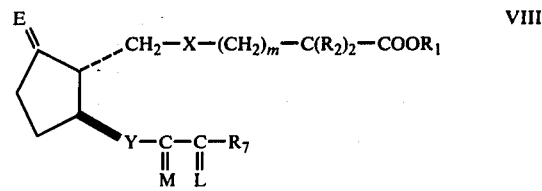

In Formula VIII, $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro, or alkyl of one to 3 carbon atoms, inclusive, or a pharmacologically acceptable cation. $R_2$ is fluoro or hydrogen. The symbol "m" is an integer 1, 2 or 3. X is $-(CH_2)_3-$, cis $-CH=CH-CH_2-$, or cis $-CH_2-CH=CH-$. E is

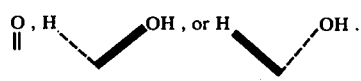

Y is $-CH_2CH_2-$ or trans $-CH=CH-$. M is

wherein $R_5$ and $R_6$ are hydrogen or methyl, with the proviso that $R_5$ is methyl only when $R_6$ is hydrogen, and $R_6$ is methyl only when $R_5$ is hydrogen. L is

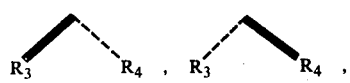

or a mixture of

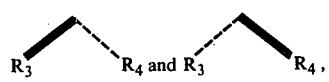

wherein $R_3$ and $R_4$, which can be the same or different, are hydrogen, methyl, or fluoro, with the proviso that one of $R_3$ and $R_4$ is fluoro only when the other is hydrogen or fluoro. $R_7$ is (1) $-(CH_2)_n-CH_3$, wherein n is one to 5, inclusive,

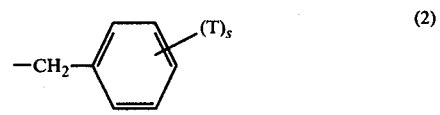

wherein T is alkyl of 1 to 3 carbon atoms, inclusive, chloro, fluoro, trifluoromethyl, or $-OR_8$, wherein $R_8$ is alkyl of 1 to 3 carbon atoms, inclusive, and s is zero to 3, inclusive, the various T's being the same or different, and no more than two T's are other than alkyl,

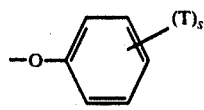

(3)

wherein T and s are as defined above, with the proviso that $R_7$ is $-(CH_2)_n-CH_3$, wherein n is as defined above, only when at least one of $R_2$, $R_3$, or $R_4$ is fluoro, with the further proviso that $R_7$ is

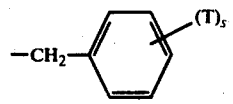

wherein T and s are as defined above, only when at least one of $R_2$, $R_3$ and $R_4$ is fluoro or X is $-CH_2-CH=$•CH$-$, and with the further proviso that $R_7$ is

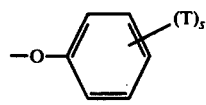

wherein T and s are as defined above, only when $R_3$ and $R_4$ are hydrogen or methyl, being the same or different.

Formula VIII includes the separate isomers wherein M is either

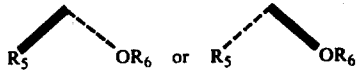

i.e. where $-OR_6$ is in either natural (alpha or L) or epi (beta or D) configuration, wherein D and L relate to the absolute configuration of D- or L-glyceraldehyde using the standard Fischer convention. See M. Hamberg, Advan. Biosci., 9, 847 (1973). Referring to the prostanoic acid atom numbering (Formula I above), the point of attachment corresponds to C-15, and, herein regardless of the variation in the C-1 to C-7 carbon chain, these epimers are referred to as C-15 epimers.

Formula VIII represents 11-deoxy-prostaglandin $E_2$-, 11-deoxy-4,5-cis-didehydro prostaglandin $E_1$-, 11-deoxy-prostaglandin $F_\alpha$- and 11-deoxy-prostaglandin $F_\beta$-type compounds, i.e. analogs of prostaglandin $E_2$, 4,5-cis-didehydroprostaglandin $E_1$, prostaglandin $F_\alpha$ and prostaglandin $F_\beta$ in which the 11-hydroxy is replaced by hydrogen. For example, Formula VIII represents 11-deoxy-2,2-difluoro-15-methyl-PGE$_2$ when $R_1$ is hydrogen, $R_2$ is fluoro, "m" is one, X is cis$-CH=CH-CH_2-$, E is

Y is trans $-CH=CH-$, M is

L is

and $R_7$ is $-(CH_2)_3CH_3$. Formula VIII represents 11-deoxy-16,16-difluoro-PGE$_2$, methyl ester, when $R_1$ is methyl, $R_2$ is hydrogen, "m" is one, X is cis$-CH=$•CH$-CH_2-$, E is $\overset{O}{\underset{\|}{}}$, Y is trans $-CH=CH-$, M is

L is

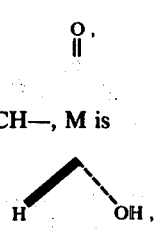

and $R_7$ is $-(CH_2)_3CH_3$. Formula VIII represents 11-deoxy-4,5-cis-didehydro-17 phenyl-18,19,20-trinor-PGE$_1$ when $R_1$ is hydrogen, $R_2$ is hydrogen, "m" is one, X is cis-$CH_2-CH=CH-$, E is $\overset{O}{\underset{\|}{}}$, Y is trans-$CH=CH-$, M is

L is

and $R_7$ is benzyl. Formula VIII represents 11-deoxy-2,2-difluoro-17-(p-fluorophenyl)-18,19,20-trinor-PGE$_2$, methyl ester, when $R_1$ is methyl, $R_2$ is fluoro, "m" is one, X is cis-$CH=CH-CH_2-$, E is $\overset{O}{\underset{\|}{}}$, Y is trans-$CH=CH-$, M is

L is

and $R_7$ is p-fluorobenzyl. Formula VIII represents 11-deoxy-2,2-difluoro-16-phenoxy-17,18,19,20-tetranor-PGE$_2$ when $R_1$ is hydrogen, $R_2$ is fluoro, "m" is one, X is cis-$CH=CH-CH_2-$, E is Y is trans-CH=CH—, M is

L is

and R$_7$ is phenoxy.

Formula VIII represents 11-deoxy-4,5-cis-didehydro-16-(m-trifluoromethyl)phenoxy-17,18,19,20-tetranor-PGE$_1$, methyl ester, when R$_1$ is methyl, R$_2$ is hydrogen, "m" is one, X is cis-CH$_2$—CH=CH—, E is

Y is trans-CH=CH—, M is

L is

and R$_7$ is m-(trifluoromethyl)phenoxy.

An alternate name for 11-deoxy-PGE$_2$ is 10,11-dihydro-PGA$_2$. These compounds may also be named as prostanoic acid derivatives. For example, 11-deoxy-PGE$_2$ is (5Z, 13E, 15S)-15-hydroxy-9-oxoprosta-5,13-dienoic acid.

As in the case of Formulas II to VII, Formula VIII wherein M is

i.e. wherein the C-15 hydroxyl or ether group is attached to the side chain in alpha configuration are each intended to represent optically active prostanoic acid derivatives with the same absolute configuration as PGE$_1$ obtained from mammalian tissues.

Also included within this invention are the 15-epimer compounds of Formula VIII wherein M is

These are identified hereinafter as "15-epi" compounds by the appropriate prefix in the name. For example, "11-deoxy-15-epi-16,16-difluoro-PGE$_2$, methyl ester", identifies the 15-epimeric compound corresponding to the Formula VIII example above except that it has the beta configuration at C-15 instead of the natural alpha configuration of 11-deoxy-PGE$_1$.

The Formula VIII plus its mirror image describes a racemic compound within the scope of this invention.

For convenience hereinafter, such a racemic compound is designated by the prefix "racemic" ("rac" or "dl") before its name; when that prefix is absent, the intent is to designate an optically active compound represented by the Formula VIII.

With regard to R$_1$ of Formula VIII, examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

The novel 11-deoxy PG analogs of this invention correspond to the prostaglandins described above, in that the novel PG analogs exhibit prostaglandin-like activity. Specifically, the 11-deoxy-PGE-, PGF$_\alpha$- and PGF$_\beta$-type compounds of this invention respectively correspond to the PGE, PGF$_\alpha$ and PGF$_\beta$ compounds described above, in that these novel PGE-, PGF$_\alpha$- and PGF$_\beta$-type compounds are useful for each of the above described purposes for which the PGE, PGF$_\alpha$ and PGF$_\beta$ compounds are used, and are respectively used in the same manner as the PGE, PGF$_\alpha$ and PGF$_\beta$ compounds, as described above.

The prostaglandins described above are all potent in causing multiple biological responses even at low doses. Moreover, for many applications these prostaglandins have an inconveniently short duration of biological activity. In striking contrast, the novel prostaglandin analogs of this invention are substantially more selective with regard to potency in causing prostaglandin-type responses, and have a substantially longer duration of biological activity.

Accordingly, each of the novel prostaglandin analogs of this invention is surprisingly and unexpectedly more useful than one of the corresponding prostaglandins, described above, for at least one of the pharmacological purposes indicated for the corresponding prostaglandin, because each of the novel prostaglandin analogs has a different and narrower spectrum of biological potency than the corresponding prostaglandin, and therefore is more specific in its activity and causes similar and fewer undesired side effects than when the corresponding prostaglandin is used for the same purpose. Moreover, because of its prolonged activity, fewer and smaller doses of the novel prostaglandin analog are frequently used to obtain the desired result.

Because of their unique chemical structure, the novel prostaglandin analogs of this invention are less sensitive to dehydration or rearrangement than the PGE-type prostaglandins and enjoy increased chemical stability and longer shelf life.

To obtain the optimum combination of biological response specificity, potency, and duration of activity, certain compounds within the scope of Formula VIII are preferred. With reference to the definitions given above, it is preferred that "m" be the integers one or 3. It is especially preferred that "m" be one. It is further preferred that M be

When $R_7$ is —$(CH_2)_n$—$CH_3$, it is preferred that "n" be 3. When $R_7$ is

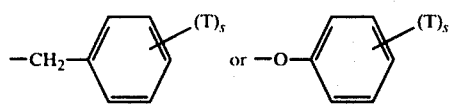

it is preferred that "s" be zero or one and T be fluoro, chloro or trifluoromethyl, especially m- or p-fluoro, m- or p-chloro and m- or p-trifluoromethyl. When one of $R_5$ or $R_6$ is methyl, it is preferred that both $R_3$ and $R_4$ be hydrogen. When one or both of $R_3$ and $R_4$ are methyl or fluoro, it is preferred that both of $R_5$ and $R_6$ be hydrogen. When $R_7$ is —$(CH_2)_n$—$CH_3$, it is preferred that at least one of $R_3$, $R_4$, $R_5$ annd $R_6$ be other than hydrogen. When E is

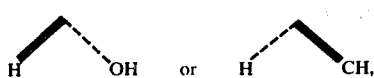

those compounds wherein E is

are preferred.

Another advantage of the novel compounds of this invention, especially the preferred compounds defined hereinabove, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The 11-deoxy-prostaglandin analogs encompassed by Formula VIII, including their alkanoates, are used for the purposes described above in the free acid form, in ester form, or in pharmacologically acceptable salt form. When the ester form is used, the ester is any of those within the above definition of $R_1$. However, it is preferred that the ester be alkyl of one to 12 carbon atoms, inclusive. Of those alkyl, methyl and ethyl are especially preferred for optimum absorption of the compound by the body or experimetal animal system; and straight-chain octyl, nonyl, decyl, undecyl, and dodecyl are especially preferred for prolonged activity in the body or experimental animal.

Pharmacologically acceptable salts of these Formula VIII compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methyl-hexylamine, declyamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, 1-adamantanamine and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like. Salts yielding crystalline PG-type compounds such as 1-adamantanamine salts, are preferred.

Examples of suitable pharmocologically acceptable quaternary ammonium cations are tetramethylammonium, tetraethylammonium, benzyltrimethylammonium, phenyltriethylammonium, and the like.

The compounds encompassed by Formula VIII are used for the purposes described above in free hydroxy form or also in the form wherein the hydroxy moieties are transformed to lower alkanoate moieties, e.g., —OH to —OCOCH$_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

As discussed above, the compounds of Formula VIII are administered in various ways for various purposes; e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_1$ in the Formula VIII compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers, are used for oral sublingual administration. For rectal or vaginal administration suppositories prepared as known in the art are used. For tissue implants, a sterile tablet or silicone rubber capsule or other object containing or impregnated with the substance is used.

A number of 11-deoxy prostaglandin compounds are reported in the literature. P. Crabbe and A. Guzman, Tetrahedron Lett. No. 2, 115, 1972, have reported the synthesis of dl-11-deoxy-PGE$_2$. dl-11-Deoxy-PGF$_{2\alpha}$ is also described in the same publication. Belgian Pat. No. 766 521 (Derwent No. 72021S) issued to Roussel-Uclaf claims 15α-hydroxy-9-oxo-5-cis-13-trans-prostadienoic acid (11-deoxy-PGE$_2$), its methyl ester, and its sodium salt. That patent also claims compounds of the general formula

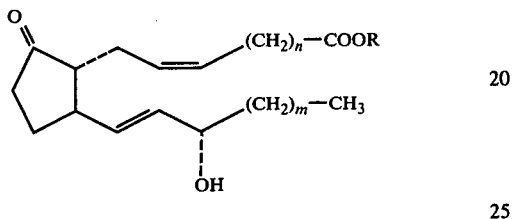

in which R represents hydrogen or lower alkyl, n is 2, 3, or 4, and m is 3, 4, or 5, including certain salts. See also Belgium Pat. No. 784 809 (Derwent No. 81307T), Netherlands Pat. Nos. 73 01094 (Derwent No. 46023U), 73 05303 (Derwent No. 66606U) and 72 08955 (Derwent No. 03130U).

The 11-deoxy prostaglandin analogs encompassed by Formula VIII are produced by the reactions and procedures described and exemplified hereinafter.

Reference to Chart A herein will make clear the process steps starting in Chart A with the aldehyde of Formula IX to provide PGE$_2$ compound of Formula XVI. The aldehyde of Formula IX is known in the art. See Crabbe et al., Tetrahedron Letters, No. 2, 115 (1972). This procedure is done by steps known in the art. See E. J. Corey et al., J. Am. Chem. Soc. 91, 5675 (1969).

CHART A

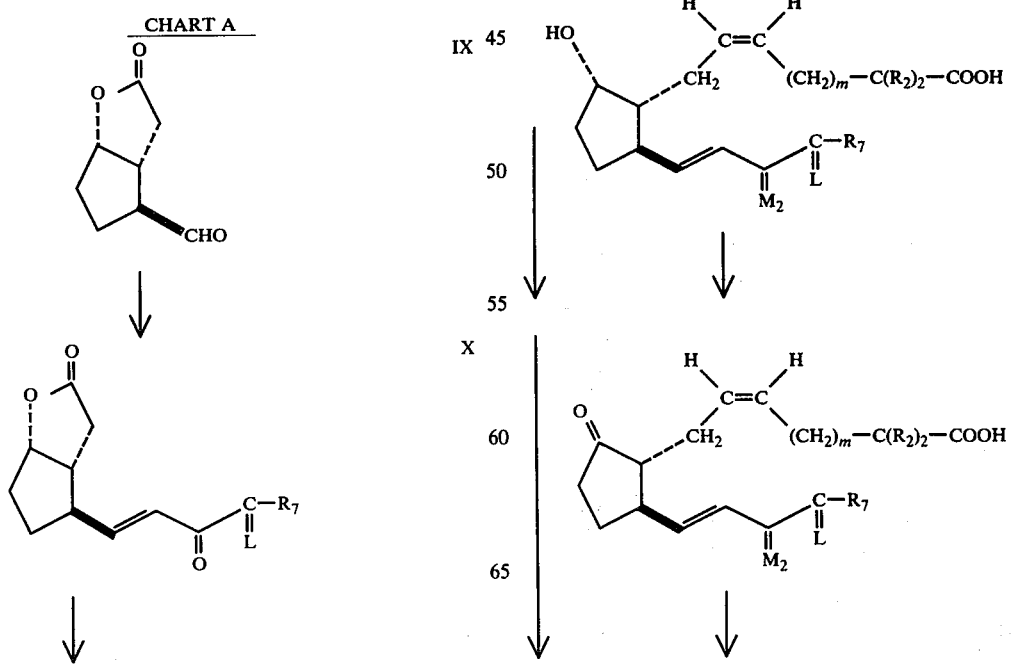

-continued

CHART A

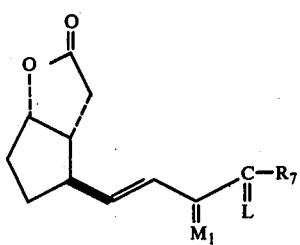
XI

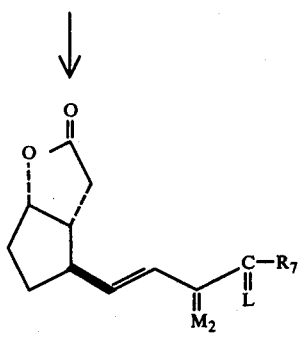
XII

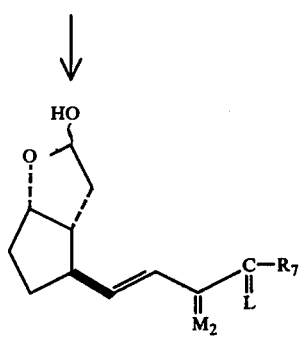
XIII

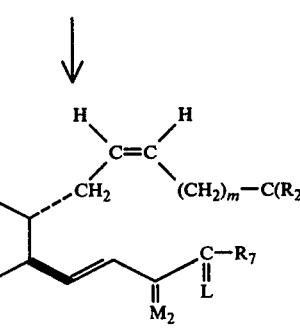
XIV

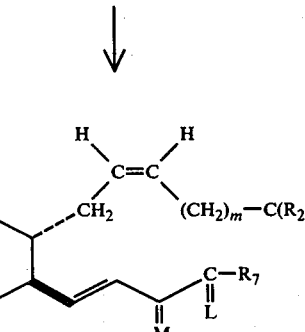
XV

-continued
CHART A

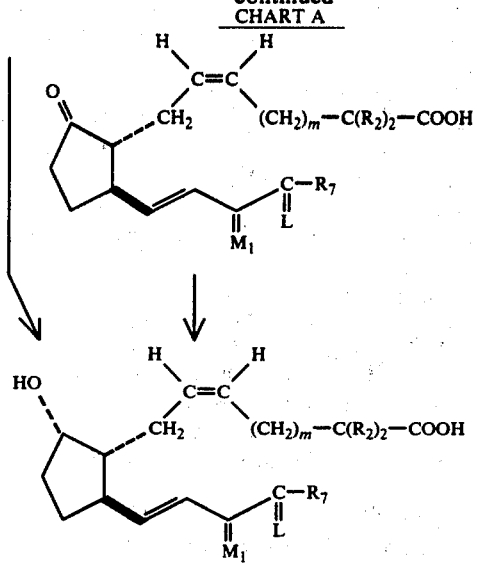

In Chart A, "m", $R_2$, L and $R_7$ are as defined above; $M_1$ is either

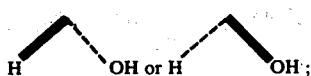

and $M_2$ is

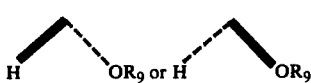

wherein $R_9$ is a "blocking group" which is defined as any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the prostaglandin-like products. Several blocking groups are known in the art, e.g. tetrahydropyranyl and substituted tetrahydropyranyl (see Corey, Proceedings of the Robert A. Welch Foundation Conferences on Chemical Research, XII, Organic Synthesis, pp. 55–79 (1969)). Those blocking groups which have been found useful include (a) tetrahydropyranyl; (b) tetrahydrofuranyl; or (c) a group of the formula

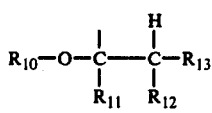

wherein $R_{10}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{11}$ and $R_{12}$ are the same or different, being hydrogen, alkyl of one to 4 carbon atoms, inclusive, phenyl or phenyl substituted with one, 2, or 3 alkyl of one to 4 carbon atoms, inclusive, or, when $R_{11}$ and $R_{12}$ are taken together, —$(CH_2)_b$— or —$(CH_2)_c$—O—$(CH_2)_d$— wherein b is 3, 4, or 5, c is one, 2, or 3, and d is one, 2, or 3 with the proviso that c plus d is 2, 3, or 4, and wherein $R_{13}$ is hydrogen or phenyl.

The Formula X compound is obtained by Wittig alkylation of IX, using the sodio derivative of an appropriate 2-oxophosphonate having the formula

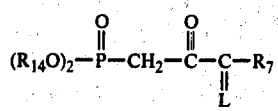

wherein $R_{14}$ is alkyl of one to 8 carbon atoms, especially methyl. The trans enone lactone is obtained sterospecifically (see D. H. Wadsworth et al., J. Org. Chem. Vol. 30, p. 680 (1965)).

The phosphonates are prepared and used by methods known in the art. See Wadsworth et al., reference cited above. Conveniently, the appropriate aliphatic acid ester is condensed with dimethyl methylphosphonate in the presence of n-butyllithium. For this purpose, acids of the general formula

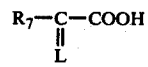

are used in the form of the lower alkyl ester, preferably methyl or ethyl esters. For this purpose methyl esters are readily formed from the acid by reaction with diazomethane. These acids are known in the art or can be prepared by methods known in the art.

Alternatively, there can be employed in the reaction, certain phosphoranes of the formula

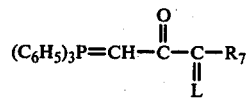

These phosphoranes are prepared and used by methods known in the art. Conveniently the appropriate ketone compound of the formula

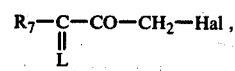

wherein Hal is chloro, bromo or iodo, is condensed with triphenylphosphine and the condensation product is treated with alkali to produce the desired phosphorane compound. The haloketone starting compound is prepared in a known way.

The formula XI compound is obtained as a mixture of alpha and beta hydroxy isomers by reduction of X. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy) aluminum hydride, metal trialkoxy borohydrides, e.g., sodium trimethoxyborohydride, lithium borohydride, and in those situations in which carbon-carbon double bond reduction is not a problem, the boranes, e.g., disiamylborane (bis-3-methyl-2-butylborane).

For production of natural-configuration prostaglandins, the alpha form of the Formula XI compounds is separated from the beta isomer by silica gel chromotography using methods known in the art.

The Formula XII lactone is obtained by replacing the hydrogen atoms of the hydroxyl groups of XI with a blocking group. When the blocking group is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in large excess, preferably 1.2 to 20 times theory. The reaction is carried out at about 20–50° C.

When the blocking group is of the formula

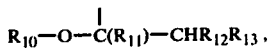

as defined above, the appropriate reagent is a vinyl ether, e.g. isobutyl vinyl ether or any vinyl ether of the formula

wherein $R_{10}$, $R_{11}$, $R_{12}$, and $R_{13}$ are as defined above; or an unsaturated cyclic or heterocyclic compound, e.g. 1-cyclohexen-1-yl methyl ether

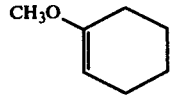

or 5,6-dihydro-4-methoxy-2H-pyran

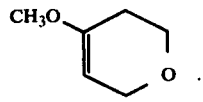

See C. B. Reese et al., J. Am. Chem. Soc. 89, 3366 (1967). The reaction conditions for such vinyl ethers and unsaturates are similar to those for dihydropyran above.

The Formula XIII lactol is obtained on reduction of lactone XII without reducing the ethylenic group. For this purpose, diisobutylaluminum hydride is used as known in the art. The reduction is preferably done at −60 to −78° C.

The stereochemistry at the C-15 position is preserved in transforming XI to XII to XIII. For example, a 15β-epimer compound XI yields a 15β-epimer compound XIII.

The Formula XIV compound is obtained from the Formula XIII lactol by the Wittig reaction, using a Wittig reagent derived from the appropriate ω-carboxyalkyltriphenylphosphonium bromide, HOOC—($R_2$)$_2$C—($CH_2$)$_m$—$CH_2$—$P(C_6H_5)_3$Br, and sodio dimethylsulfinylcarbanide. The phosphonium compounds are known in the art or are readily available, e.g. by reaction of an ω-bromoaliphatic acid with triphenylphosphine.

When $R_2$ is fluoro, the corresponding ω-bromoaliphatic acid used to prepare the phosphonium compound can be prepared, for example, by reducing methyl furoate to methyltetrahydrofuroate by hydrogenation using a 5 percent palladium on charcoal catalyst. The methyltetrahydrofuroate is converted to methyl-2-acetoxy-5-bromo-pentanoate by reaction with HBr and acetic anhydride, under anhydrous conditions. The methyl-2-acetoxy-5-bromo-pentanoate is transformed to the corresponding alcohol methyl-2-hydroxy-5-bromo-pentenoate by treatment with ice cold methanol saturated with HBr and then the alcohol is transformed to the corresponding ketone methyl-2-oxo-5-bromo-pentanoate by reaction with Jones reagent. The ketone is transformed to methyl-2,2-difluoro-5-bromo-pentanoate by reaction with molybdenum hexafluoride in boron trifluoride (Fluoreze M by PCR Incorporated) at −35° to 45° C and that methyl ester is hydrolyzed in aqueous HBr to yield 2,2-difluoro-5-bromo-pentanoic acid.

The Formula XIV compound can be converted to the corresponding Formula XV compound by the Jones regent or Collins reagent, which is in turn converted to the PGE$_2$ compound XVI by mild acid hydrolysis.

The Formula XIV compound can be converted to the PGF$_2$ compound XVII by removal of the blocking group R$_9$ by mild acid hydrolysis, for example using acetic acid.

Referring to Chart B, there is shown the transformation of lactone XI to 15-methyl ether-PGE$_2$-type products of Formula XX. In chart B, "m", M$_1$, R$_2$, L, and R$_7$ have the same meanings as above. M$_3$ is either

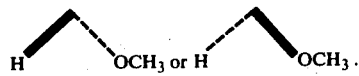

CHART B

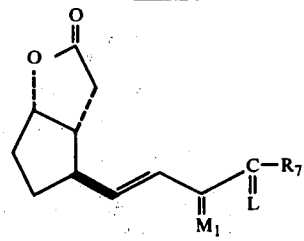

XI

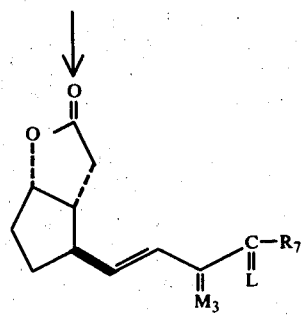

XVIII

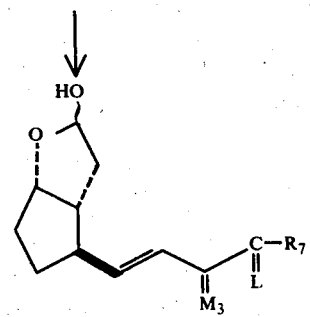

XIX several steps

-continued
CHART B

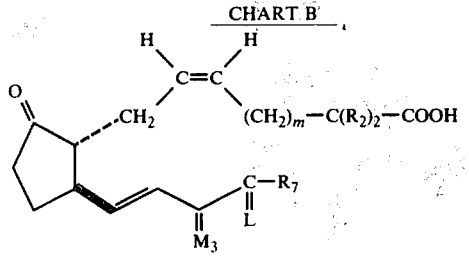

The starting materials are available from the steps of Chart A above or are readily available by methods known in the art.

The Formula XVIII compound is prepared by alkylation of the side-chain hydroxy of the Formula XI compound thereby replacing hydroxy with the —OCH$_3$ moiety. For this purpose, diazomethane may be employed, preferably in the presence of a Lewis acid, e.g. boron trifluoride etherate, aluminum chloride, or fluoboric acid. See Fieser et al., "Reagents for Organic Synthesis", John Wiley and Sons, Inc. N.Y. (1967), p. 191. The reaction is carried out of mixing a solution of the diazoalkane in a suitable inert solvent, preferably diethyl ether, with the Formula XI compound. Generally the reaction proceeds at about 25° C.

Another method for the alkylation of the side chain hydroxy is by reaction with an alcohol in the presence of boron trifluoride etherate. Thus, methanol and boron trifluoride etherate yield the methyl ether. The reaction is done at about 25° C. and is conveniently followed with thin layer chromotography (TLC).

Another method for the alkylation of the side-chain hydroxy is by the reaction of an alkyl halide, e.g. methyl iodide, in the presence of a metal oxide or hydroxide, e.g. barium oxide, silver oxide, or barium hydroxide. An inert solvent may be beneficial, for example benzene or dimethylformamide. The reactants are preferably stirred together and maintained at temperatures of 25–75° C.

Still another method is by first converting the hydroxy to mesyloxy (i.e. methanesulfonate) or tosyloxy (i.e. toluenesulfonate) and thence transforming the mesyloxy or tosyloxy to the —OCH$_3$ moiety by reaction with a metal alkoxide, in an excess of methanol. The mesylate or tosylate is prepared by reaction of the Formula XI intermediate with either methanesulfonyl chloride or toluenesulfonyl chloride in pyridine. Thereafter, the mesylate or tosylate is mixed with the appropriate potassium or sodium methoxide or methanol in pyridine, the reaction proceding smoothly at about 25° C. An equivalent amount of the methoxide based on the mesylate is preferred to avoid side reactions. This method, however, results in some isomerization at C-15, as well as poor yield in many cases.

The Formula XIX compound is then obtained in the conventional manner, for example by low temperature reduction with diisobutylaluminum hydride as discussed above for Chart A. The final 15-methyl ether-PGE$_2$ product XX is obtained from XIX by the same reactions and conditions discussed above for the steps of Chart A.

Referring to Chart C, there is shown the transformation of lactone X to lactol XXIII useful for preparing 15-methyl-PG-type products. In Chart C, M$_4$ is ether

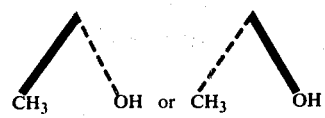

M$_5$ is either

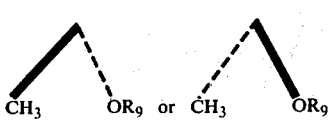

wherein R$_9$ is as defined above.

For the starting material X refer to Chart A and the discussion pertaining thereto. Intermediate XXI is obtained by replacing the side-chain oxo with M$_4$ by a conventional Grignard reaction, employing CH$_3$MgHal. Next the hydrogen atom of the hydroxyl group is replaced with blocking group R$_9$ following the procedures of Chart A. Finally lactol XXIII is obtained by reduction of lactone XXII in the same manner discussed above for Chart A.

CHART C

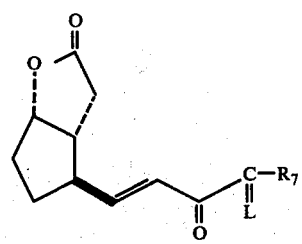

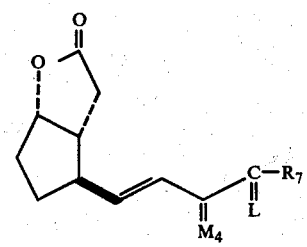

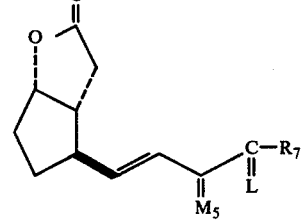

-continued
CHART C

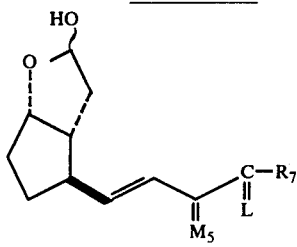
XXIII

The 15-alkyl-PGE and PGF-type products of this invention are obtained from lactone XXII either with or without isolating the Formula XXIII lactol, following the procedures discussed above for Chart A. The 15-alpha and 15-beta isomers are separated by conventional means, for example silica gel chromotography of the corresponding methyl esters at the final product stages.

Referring to Chart D, there is shown the transformation of lactol XIII to 4,5-didehydro-PGF$_{1\alpha}$ and 4,5-didehydro-PGE$_1$-type compounds. In Chart D, "m", R$_2$, M$_1$, M$_2$ and R$_7$ have the same meanings as above. L$_1$ is

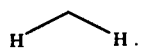

M$_6$ is either

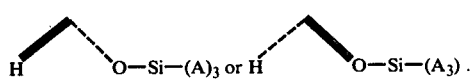

A is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive. R$_{15}$ is alkyl of 4 to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive. R$_{16}$ is R$_1$ as defined above or silyl of the formula —Si—(A)$_3$ wherein A is as defined above. The various A's of a —Si—(A)$_3$ moiety are alike or different. For example, a —Si—(A)$_3$ can be trimethylsilyl, dimethylpropylsilyl, dimethylphenylsilyl, or methylphenylbenzylsilyl. Examples of alkyl of one to 4 carbon atoms, inclusive, are methyl, ethyl, propyl, isopropyl, butyl, isobutyl, sec-butyl, and tert-butyl.

CHART D

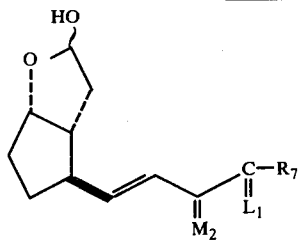
XIII

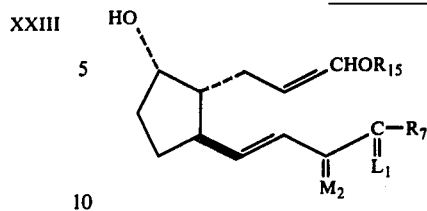
XXIV

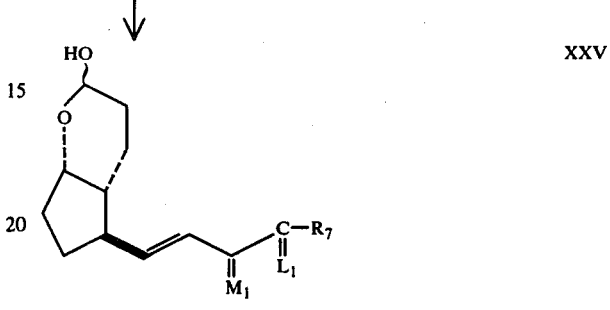
XXV

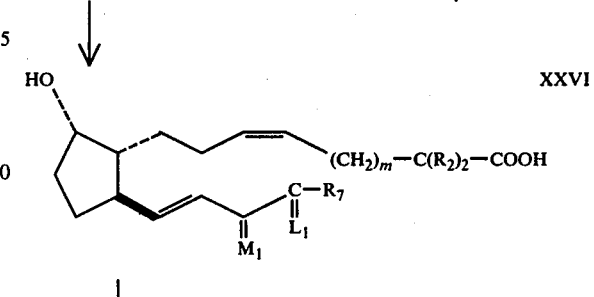
XXVI

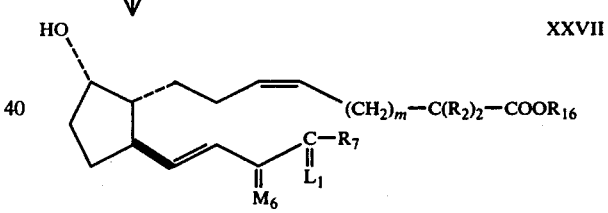
XXVII

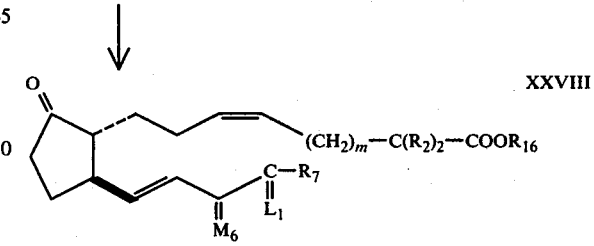
XXVIII

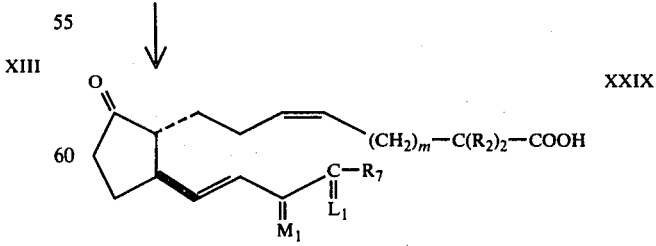
XXIX

Examples of aralkyl of 7 to 12 carbon atoms, inclusive, are benzyl, phenethyl, α-phenylethyl, 3-phenylpropyl, α-naphthylmethyl, and 2-(β-naphthyl)ethyl. Examples of phenyl substituted with one or 2 fluoro, chloro, or alkyl of one to 4 carbon atoms, inclusive, are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

The Formula XIII lactol is condensed to form the Formula XXIV enol ethers. For this purpose, an alkoxymethylenetriphenylphosphorane is useful. See, for example, Levine, J. Am. Chem. Soc. 80, 6150 (1958). The reagent is conveniently prepared from a corresponding quaternary phosphonium halide and a base, e.g., butyl lithium or phenyl lithium, at a low temperature, e.g. preferably below −10° C. The Formula XIII lactol is mixed with the reagent and the condensation proceeds smoothly within the temperature range −30° C. to +30° C. At higher temperatures the ragent is unstable, whereas at low temperatures the rate of condensation is undesirably slow. Examples of the alkoxymethylenetriphenylphosphoranes preferred for forming the Formula XXIV enol ethers are methoxy-, ethoxy-, propoxy-, isopropoxy-, butoxy-, isobutoxy-, sec-butoxy-, and tert-butoxymethylenetriphenylphosphorane.

Various hydrocarbyloxymethylenetriphenylphosphoranes which can be substituted for the alkoxymethylenetriphenylphosphoranes and are therefore useful for preparing Formula XXIV intermediates wherein $R_{15}$ is hydrocarbyl, including alkoxy (of 4 to 18 carbon atoms)-, aralkoxy-, cycloalkoxy-, and aryloxymethylenetriphenylphosphoranes. Examples of these hydrocarbyloxymethylenetriphenylphosphoranes are 2-methylbutoxy-, isopentyloxy-, heptyloxy-, octyloxy-, nonyloxy-, tridecyloxy-, octadecykloxy, benzyloxy-, phenethyloxy-, p-methylphenethyloxy-, 1-methyl-3-phenylpropyoxy-, cyclohexyloxy-, phenoxy-, and p-methylphenoxy-methylenetriphenyphosphorane. See, for example, Organic Reactions, Vol. 14, pages 346–348, John Wiley and Sons, Inc., N.Y., (1965).

The Formula XXIV enol ether is hydrolyzed to the Formula XXV lactol. This hydrolysis is done under acidic conditions, for example with perchloric acid or acetic acid. Tetrahydrofuran is a suitable diluent for this reaction mixture. Reaction temperatures of from 10° C. to 100° C. may be employed. The length of time required for hydrolysis is determined in part by the hydrolysis temperature. With acetic acid-water-tetrahydrofuran at about 60° C., several hours are sufficient.

The Formula XXV lactol is transformed to the Formula XXVI PGF-type products by condensation with a Wittig reagent derived from 3-carboxypropyltriphenylphosphonium halide and sodio methylsulfinylcarbanide. Dimethylsulfoxide is conveniently used as a solvent, and the reaction may be done at about 25° C.

The various Formula XXIV and XXV intermediates are useful directly as produced or they may be subjected to purification procedures, for example silica gel chromatography or recrystallization.

The Formula XXVI PGF-type compound can be transformed to the corresponding PGE-type compound of Formula XXIX. For this purpose the Formula XXVI compound is selectively silylated at the C-15 position, by choice of reagents and conditions. Silylating agents are known in the art. See, for example, Pierce, "Silylation of Organic Compounds," Pierce Chemical Co., Rockford, Ill. (1968). Silylating agents of the type $(A)_3$-SiN(G)$_2$, i.e. substituted silylamines wherein A is as defined above and G has the same definition as A, being the same or different, are useful for the above purpose at temperatures below about −25° C. A preferred temperature range is about −35° to −50°. At higher temperatures some silylation of C-9 hydroxyl groups as well as the C-15 hydroxyl group occurs, whereas at lower temperatures the rate of silylation is undesirably slow. Examples of silylamine type silylating agents suitable for forming the Formula XXVII intermediates include pentamethylsilylamine, pentaethylsilylamine, N-trimethylsilyldiethylamine, 1,1,1-triethyl-N,N-dimethylsilylamine, N,N-diisopropyl-1,1,1-trimethylsilylamine, 1,1,1-tributyl-N,N-dimethylsilylamine, N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine. The reaction is carried out with exclusion of atmospheric moisture, for example, under a nitrogen atmosphere. It is conveniently done in a solvent such as acetone or dichloromethane, although the silylating agent itself, when used in excess, may also serve as a liquid medium for the reaction. The reaction ordinarily is completed in a few hours, and should be terminated when the C-15 hydroxyl group is silylated, to avoid side reactions. The progress of the reaction is conveniently monitored by thin-layer chromatography (TLC), utilizing methods known in the art.

An excess of the reagent over that stoichiometrically required is used, preferably at least a four-fold excess. The -COOH moiety may be partially or even completely transformed to —COO—Si—(A)$_3$, additional silylating agent being used for this purpose. Whether or not this occurs is immaterial for the success of the process, since —COOH groups are not changed by the subsequent steps and —COO—Si(A)$_3$ groups are easily hydrolyzed to —COOH groups.

The Formula XXVII silyl ether intermediate is oxidized to the Formula XXVIII compound. Oxidation reagents useful for this transformation are known in the art. An especially useful reagent for this purpose is the Collins reagent, i.e. chromium trioxide in pyridine. See J. C. Collins et al., Tetrahedron Lett., 3363 (1968). Dichloromethane is a suitable diluent for this purpose. A 6-8 fold excess of the oxidant beyond the amount necessary to oxidize the C-9 secondary hydroxy group of the Formula XXVII intermediate is used. Reaction temperatures of below 20° C. should be used. Preferred reaction temperatures are in the range −10° to +10° C. The oxidation proceeds rapidly and is usually complete in about 5 to 20 minutes. Finally all silyl groups of the Formula XXVIII intermediate are removed by hydrolysis, thereby forming the Formula XXIX PGE-type products. This hydrolysis is carried out by prior art procedures known to be useful for transforming silyl ethers and silyl esters to alcohols and carboxylic acids, respectively. See, for example, Pierce, cited above, especially p. 447 thereof. A mixture of water and sufficient of a water-miscible organic diluent to give a homogeneous hydrolysis reaction mixture represents a suitable reaction medium. Addition of a catalytic amount of an organic or inorganic acid hastens the hydrolysis. The length of time required for the hydrolysis is determined in part by the hydrolysis temperature. With a mixture of water and methanol at 25° C., several hours is usually sufficient for hydrolysis. At 0° C., several days is usually necessary. The Formula XXIX PGE-type product is isolated by conventional means.

Referring to Chart E, there is shown the transformation of lactol XXV to 4,5-didehydro-PGF$_{1\alpha}$ and 4,5-didehydro-PGE$_1$-type compounds. In Chart E, "m", R$_2$, M$_1$, M$_2$, L and R$_7$ have the same meanings as above.

The Formula XXV lactol is transformed to acid XXX, for example, by reaction with silver oxide. Tetrahydrofuran is a suitable diluent for this reaction mixture. Reaction temperatures of from 10° to 100° C. may be employed. The reaction ordinarily is completed within a few hours.

The Formula XXX acid is trnasformed to the Formula XXXI lactone by reaction with pyridine hydrochloride. Dichloromethane is a suitable solvent for this reaction. Reaction temperatures of 15° to 40° C. may be employed. The reaction ordinarily is completed within a few hours. The reaction is carried out with exclusion of atmospheric moisture, for example, under a nitrogen atmosphere.

The Formula XXXI lactone is transformed to the 4,5-didehydro-PGF$_{1\alpha}$ Compounds XXXV and to the 4,5-didehydro-PGE$_1$ compounds XXXIV by steps corresponding to those employed for transforming lactone XI to Formula XVI PGE$_2$ compound and Formula XVII PGF$_2$ compound, as described for Chart A.

Referring to Chart F, there is shown the transformation of the Formula XIX compound to 4,5-didehydro-11-deoxy-15-methyl ether-PGF$_{1\alpha}$ and 4,5-didehydro-11-deoxy-15-methyl ether-PGE$_1$-type compounds. In Chart F, "m", R$_2$, M$_3$, L, R$_7$ and R$_{15}$ have the same meanings as above.

CHART E

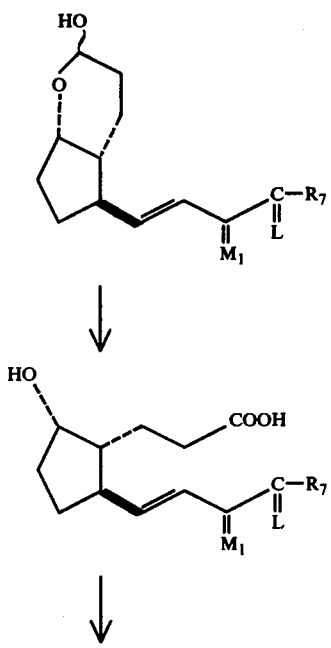
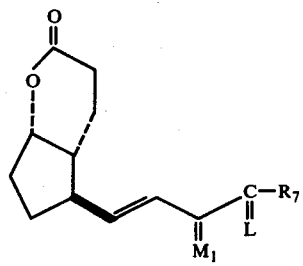
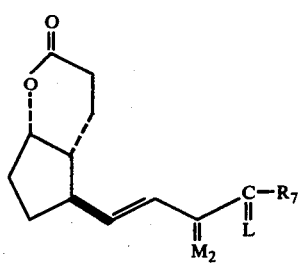
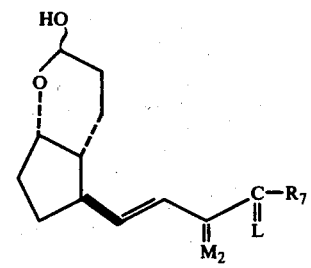
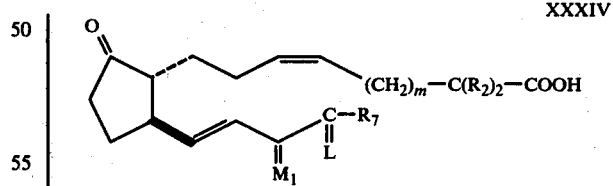
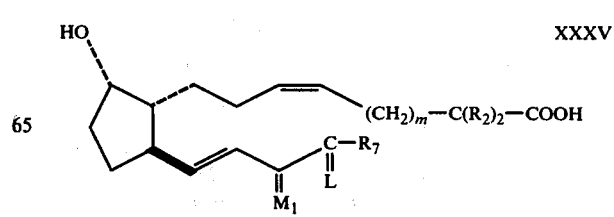

CHART F

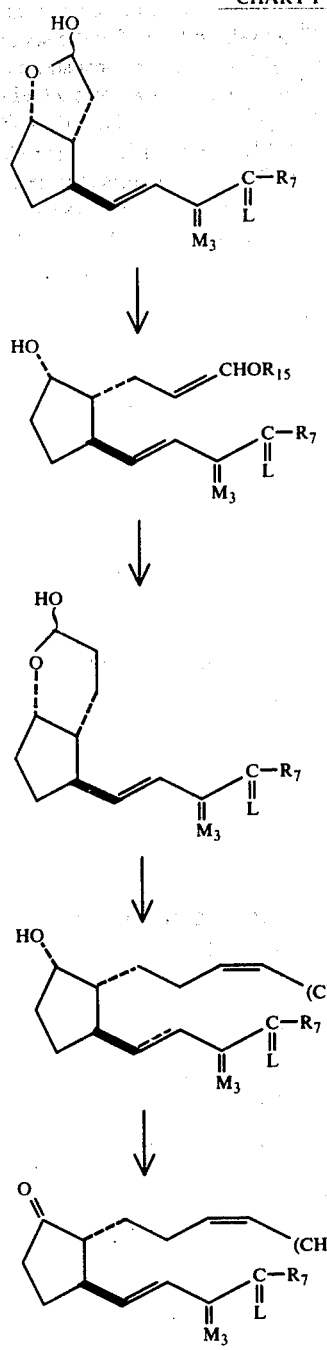

The procedures of Chart D are followed, except that the Formula XIX compound is used as the starting material, instead of the Formula XIII compound of Chart D. Under these conditions, it is not required to form a silylated intermediate, such as the Formula XXVI compound of chart D. Rather, in Chart F, the Formula XXXVIII PGF-type compound can be directly oxidized to form the Formula XXXIX PGE-type product.

Referring to Chart G, there is shown the transformation of the Formula XXVI compound to 4,5-didehydro-11-deoxy-15-methyl-PGF$_{1\alpha}$compounds. In Chart G, "m", $R_2$, A, $M_1$, L and $R_7$ have the same meanings as above.

In the first step of Chart G, the Formula XXVI compounds are oxidized to the intermediate Formula LX 15-oxo acids. For this purpose, reagents such as 2,3-dichloro-5,6-dicyano-1,4-benzoquinone, activated manganese dioxide, or nickel peroxide are used, according to procedures known in the art. See Fieser et al., "Reagents for Organic Synthesis," John Wiley and Sons, Inc., New York, N.Y., (1967) pp. 215, 637, and 731.

The Formula XL 15-oxo compounds are transformed to silyl derivatives of Formula XLI by procedures known in the art. See, for example, Pierce, "Silylation of Organic Compounds," Pierce Chemical Co., Rockford, Ill. (1968). The 9-hydroxy group of the Formula XL reactants are thereby transformed to —O—Si(A)$_3$ moieties wherein A is as defined above, and sufficient of the silylating agent is used for that purpose according to known procedures. The —COOH moiety thereby defined is simultaneously transformed to —COO—Si(A)$_3$, additonal silylating agent being used for this purpose. This latter transformation is aided by excess silylating agent and prolonged treatment.

CHART G

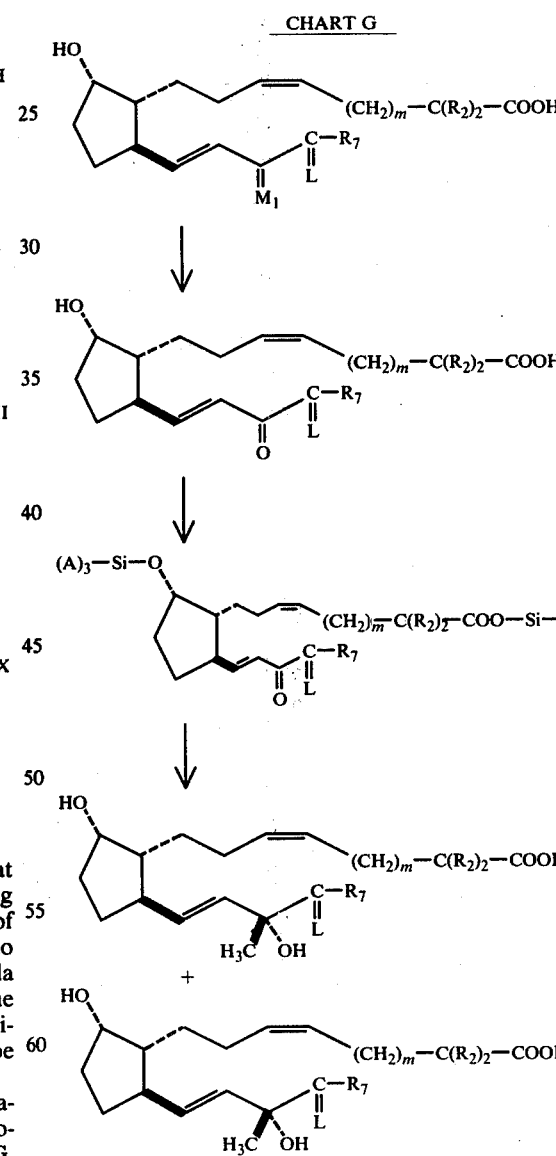

The necessary silylating agent for these transformations are known in the art or are prepared by methods known in the art. See, for example, Post, "Silicones and Other Organic Silicon Compounds," Reinhold Publishing Corp., New York, N.Y. (1949).

The Formula XLI compound is transformed to the final 15-methyl substituted compounds of Formulas XLII and XLIII by first reacting the silyl compound with a Grignard reagent of the formula CH₃MgHal, wherein Hal is chloro, bromo, or iodo. For this purpose, it is preferred that Hal be bromo. This reaction is carried out by the usual procedure for Grignard reactions, using diethyl ether as a reaction solvent and saturated aqueous ammonium chloride solution to hydrolyze the Grignard complex. The resulting disilyl compound is then hydrolyzed with water to remove the silyl groups. For this purpose, it is advantageous to use a mixture of water and sufficient of a water-miscible solvent, e.g., ethanol to give a homogenous reaction mixture. The hydrolysis is usually complete in 2 to 6 hours at 25° C., and is preferably carried out in an atmosphere of an inert gas, e.g., nitrogen or argon.

The mixture of 15-α and 15-α isomers obtained by this Grignard reaction and hydrolysis is separated by procedures known in the art for separating mixtures of prostanoic acid derivatives, for example, by chromatography on neutral silica gel. In some instances, the lower alkyl esters, especially the methyl esters of a pair of 15-α and 15-β isomers are more readily separated by silica gel chromatography than are the corresponding acids. In those cases, it is advantageous to esterify the mixture of acids as described below, separate the two esters, and then, if desired, saponify the esters by procedures known in the art for saponification of prostaglandins F.

The 4,5-didehydro-11-deoxy-15-methyl-PGE-type compounds are prepared from the above-15-substituted PGF-type compounds of Formulas XLII and XLIII following the steps of Chart H. In Chart H, "m", R₂, R₁₆, L and R₇ have the same meanings as above. M₇ is

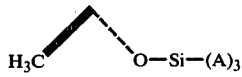

wherein A has the same meaning as above.

Following the final three steps of Chart D, using the same reagents and conditions, the Formula LIV compound is transformed to the PGE-type compounds represented by Formula XLVI.

Chart I shows the transformation of the Formula XLVII PGE-type compounds to the corresponding PGF-type compounds. In Chart I, R₁, R₂, R₇, M, L, X, Y and m are as defined above.

The various PGFα-type and PGFβ-type compounds encompassed by Formula XLVIII are prepared by carbonyl reduction of the corresponding PGE-type compounds. For example, carbonyl reduction of 11-deoxy-2,2-difluoro-15-methyl-PGE₂ gives a mixture of 11-deoxy-2,2-difluoro-15-methyl-PGF₂α and 11-deoxy-2,2-difluoro-15-methyl-PGF₂β.

These ring carbonyl reductions are carried out by methods known in the art for ring carbonyl reductions of known prostanoic acid derivatives. See, for example, Bergstrom et al, Arkiv Kemi 19, 563 (1963), Acta Chem. Scand. 16, 969 (1962), and British Specification No. 1 097 533. Any reducing agent is used which does not react with carbon-carbon double bonds or ester groups. Preferred reagents are lithium (tri-tertbutoxy) aluminum hydroxide, the metal borohydrides, e.g., sodium, potassium and zinc borohydrides and metal trialkoxy borohydrides, e.g., sodium trimethoxyborohydride.

The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research 5, 117 (1964). Alternatively used are partition chromatographic procedures, both normal, reversed phase, preparative thin layer and column chromatography, and countercurrent distribution procedures.

CHART H

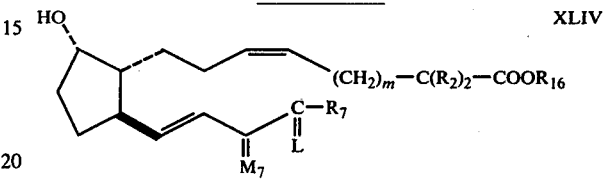

XLIV

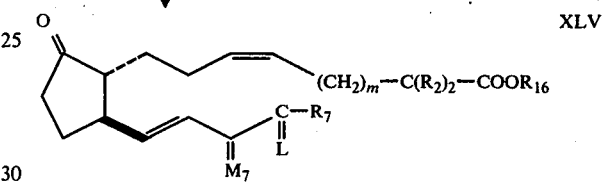

XLV

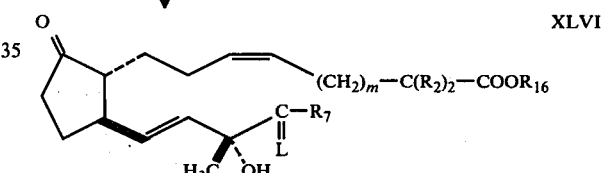

XLVI

CHART I

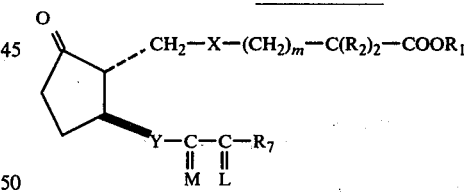

XLVII

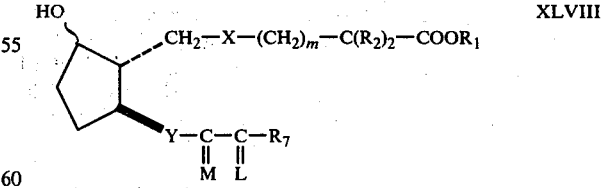

XLVIII

The 13,14-dihydro-PG-type compounds of Formula VIII, wherein Y is —CH₂CH₂— and X is cis—CH=CH—CH₂—, or cis —CH₂—CH=CH—, are prepared by reducing the Formula XI compound of Charts A and B, the Formula XXI compound of Chart C, the Formula XXV compound of Chart D, or the Formula XXXVII compound of Chart F, to the corresponding 13,14-dihydro compound according to the process steps of Chart J. The respective thus-obtained 13,14-dihydro compounds of Formulas XLIX to LII are then transformed to the 13,14-dihydro-PG-type compounds by the remaining steps of Charts A-G, respectively. In Chart J, $M_1$, $M_3$, $M_4$, L and $R_7$ are as defined above.

Reducing agents useful for effecting the transformations shown in Chart J are known in the art. Thus, hydrogen is used at atmospheric pressure or low pressure with catalysts such as palladium on charcoal or platinum oxide. The respective Formulas XLIX to LII compounds are separated from their starting materials or other compounds by methods known in the art, e.g. silica gel chromatography.

Reference to Chart K will make clear the formation of the 13,14-dihydro-PG$_1$-type compounds of Formula VIII, wherein Y is —CH$_2$CH$_2$— and X is —(CH$_2$)$_3$—. In Chart K, $R_1$, $R_2$, $R_7$, E, M, L, X and m are as defined above.

CHART J

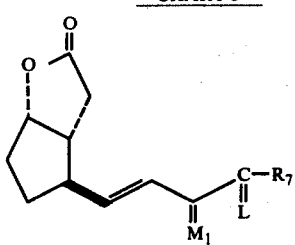

XI

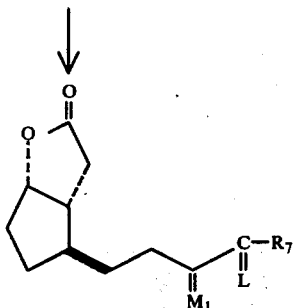

XLIX

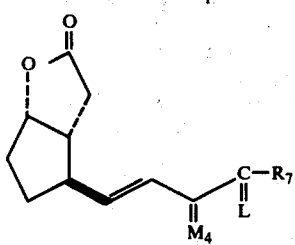

XXI

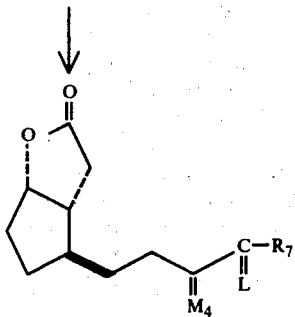

L

-continued

CHART J

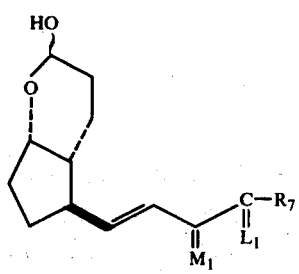

XXV

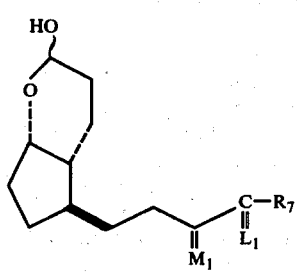

LI

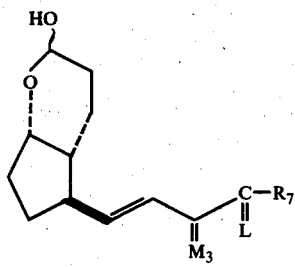

XXXVII

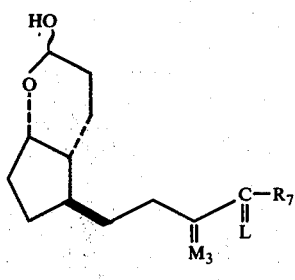

LII

CHART K

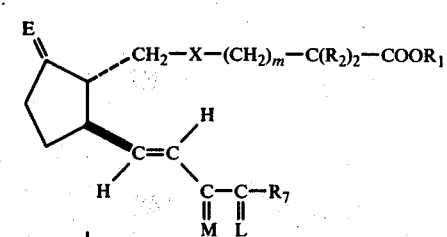

LIII

-continued
CHART K

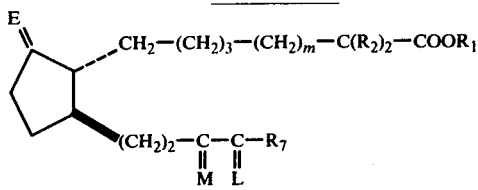

LIV

The various 13,14-dihydro-PG$_1$-type compounds are prepared by carbon-carbon double bond reduction of the corresponding PGE, PGF$_\alpha$, and PGF$_\beta$ type compounds containing a trans double bond at 13,14. A cis double bond can also be present in the carboxy-terminated side chain of the unsaturated reactant, and will be reduced at the same time to —CH$_2$CH$_2$—.

These reductions are carried out by reacting the unsaturated PGE, or PGF type compound with diimide, following the general procedure described by van Tamelen et al., J. Am. Chem. Soc, 83, 3726 (1961). See also Fieser et al., "Topics in Organic Chemistry," Reinhold Publishing Corp., New York, pp. 432–434 (1963) and references cited therein. The unsaturated acid of ester reactant is mixed with a salt of azodiformic acid, preferably an alkali metal salt such as the disodium or dipotassium salt, in the presence of an inert diluent, preferably a lower alkanol such as methanol of ethanol, and preferably in the absence of substantial amounts of water. At least one molecular equivalent of the azodiformic acid salt is used for each multiple bond equivalent of the unsaturated reactant. The resulting suspension is then stirred, preferably with exclusion of oxygen, and the mixture is made acid, advantageously with a carboxylic acid such as acetic acid. When a reactant wherein R$_1$ is hydrogen is used, the carboxylic acid reactant also serves to acidify an equivalent amount of the azodiformic acid salt. A reaction temperature in the range about 10° to about 40° C. is usually suitable. Within that temperature range, the reaction is usually complete within less than 24 hours. The desired dihydro product is then isolated by conventional methods, for example evaporation of the diluent, followed by separation from inorganic materials by solvent extraction.

The reductions are also carried out by catalytic hydrogenation. For that purpose, palladium catatlyst, especially on a carbon carrier, are preferred. It is also preferred that the hydrogenation be carried out in the presence of an inert liquid diluent, for example, methanol, ethanol, dioxane, ethyl acetate, and the like. Hydrogenation pressures ranging from about atomspheric to about 50 p.s.i., and hydrogenation temperatures ranging from about 10° to about 100° C. are preferred. The resulting fully saturated product is isolated from the hydrogenation reaction mixture by conventional methods, for example, removal of the catalyst by filtration or centrifugation, followed by evaporation of the solvent.

In all of the above-described reactions, the products are separated by conventional means from the starting materials and impurities, for example by silica gel chromatography monitored by thin-layer chromatography (TLC).

Optically active compounds are obtained from optically active intermediates according to the process steps of Charts A-K. When racemic intermediates are used in reactions corresponding to the processes of Charts A-K, inclusive, and racemic products are obtained, these racemic products may be used in their racemic form or, if preferred, they may be resolved as optically active isomers by procedures known in the art.

For example, when final compound VIII is a free acid, the dl form thereof is resolved in the d and l forms by reacting said free acid by known general procedures with an optically active base, e.g., brucine or strychine, to give a mixture of two diastereoisomers which are separated by known general procedures, e.g., fractional crystallization, to give the separate diastereoisomeric salts. The optically active acid of Formula VIII is then obtained by treatment of the salt with an acid by known general procedures.

Referring to Chart A, when a Formula XI compound is prepared by reacting a racemic compound corresponding to Formula IX with a racemic Wittig reagent, there are obtained two pairs of racemates which are separable into pairs of racemic compounds by methods known in the art, e.g. silica gel chromatography. When a racemic compound corresponding to Formula IX is reacted with an optically active isomer of the Wittig reagent, there are obtained two diastereomers corresponding to the Formula XI compound which are separated by conventional methods, e.g. by silica gel chromatography.

It is preferred that the Formula IX compound by used in the optically active form which will lead to an 11-deoxy prostaglandin analog of the natural configuration. For this purpose, there is provided a process for resolving a racemic mixture of an oxo compound of the formula

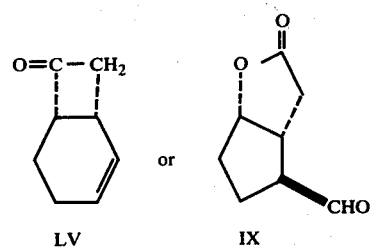

and of the mirror image thereof, which comprises the steps of (a) converting the oxo compound by reaction with an optically active ephedrine to a mixture of oxazolidine diastereomers, (b) separating at least one oxazolidine diastereomer from said mixture, (c) hydrolyzing said oxazolidine to free the optically active oxo compound, and (d) recovering said optically active oxo compound.

In carrying out the resolution of the Formula LV ketone, there is prepared an oxazolidine by reaction of the ketone with an optically active ephedrine, e.g. d- or l-ephedrine, or d- or l-pseudoephedrine. Approximately equimolar quantities of the reactants are employed in a solvent such as benzene, isopropyl ether, or dichloromethane. The reaction proceeds smoothyl over a wide range in temperature, for example 10° to 80° C., although for some reactants the range 20° to 30° C. is preferred for convenience. The reaction occurs quickly, within minutes, whereupon the solvent is removed, preferably under vacuum. The product consists of the diastereomers of the ketone-ephedrine product, i.e. the oxazolidines. At least one of the diastereomers is separated by methods known in the art, including crystallization and chromatography. In this resistance, crystallization is used as the preferred method. Repeated recrystallization of the thus-obtained solid oxazolidine from a suitable solvent, e.g., isopropyl ether, yields one of the diastereomers in substantially pure form. The oxazolidine is then hydrolyzed by procedures known in the art to release the ketone.

The mother liquor from the recrystallized diastereomer contains the optical isomer having opposite configuration. A preferred method for isolating this second diastereomer, however, is to prepare the oxazolidine of the racemic ketone using ephedrine of the opposite configuration to that first employed above, and thereafter recrystallizing as above. Finally, hydrolysis and recovery yield the resolved Formula LV ketone in opposite configuration to that first obtained above.

Each optically active ketone can be converted to an aldehyde of the formula

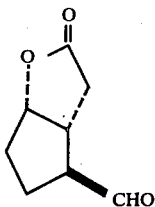

IX or the mirror image thereof, using the procedures of Corey et al., Tetrahedron Lett. 49, 4753 (1971). That ketone is especially useful which yields the Formula IX aldehyde which produces the 11-deoxy prostaglandin analogs having the natural configuration.

Likewise, the above process of resolution applied to the racemate containing the Formula IX aldehyde yields the optically active Formula IX aldehyde which produces the 11-deoxy prostaglandin analogss having the natural configuration.

As discussed above, the processes of Charts A-K, inclusive, lead variously to acids ($R_1$ is hydrogen) or to esters ($R_1$ is alkyl, cycloalkyl, aralkyl, phenyl or substituted phenyl, as defined above). When an acid has been prepared and an alkyl, cycloalkyl or aralkyl ester is desired, esterification is advantageously accomplished by interaction of the acid with the appropriate diazohydrocarbon. For example, when diazomethane is used, the methyl esters are produced. Similar use of diazoethane, diazobutane, 1-diazo-2 ethylhexane, diazodecane, diazocyclohexane and phenyldiazomethane, for example, gives the ethyl, butyl, 2-ethylhexyl, decyl and cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with diazohydrocarbon be no longer than necessary to effect the desired esterification, preferably about one to about ten minutes, to avoid undesired molecular changes. Diazohydrocarbons, are known in the art or can be prepared by methods known in the art. See, for example, Organic Reactions, John Wiley and Sons, Inc., New York, N.Y., Vol. 8, pp. 389–394 (1954).

An alternative method for esterification of the carbonyl moiety of the acid compounds comprises transformation of the free acid to the corresponding metal salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl and the like. The metal salts are prepared by conventional methods, for example, by dissolving the acid in cold dilute aqueous ammonia, evaporating the excess ammonia at reduced pressure, and then adding the stoichiometric amount of silver nitrate.

The phenyl and substituted phenyl esters of the acid compounds are prepared by silylating the acid to protect the hydroxy groups, for example, replacing each —OH with —O—Si— $(CH_3)_3$. Doing that may also change —COOH to —COO—SI—$(CH_3)_3$. A brief treatment of the silylated compound with water will change —COO—Si—$(CH_3)_3$ back to —COOH. Procedures for this silylation are known in the art and are discussed hereinabove. Then, treatment of the silylated compound with oxalyl chloride gives the acid chloride which is reacted with phenol or the appropriate substituted phenol to give a silylated phenyl or substituted phenyl ester. Then the silyl groups, e.g., —O—Si—$(CH_3)_3$ are changed back to —OH by treatment with dilute acetic acid. Procedures for these transformations are known in the art.

When the processes of Charts A-K, inclusive, yield an ester, such as where $R_1$ is methyl, the free acid products are obtained by methods known in the art. For example, the PG compounds are subjected to enzymatic hydrolysis using an esterase enzyme composition obtained by acetone extraction at low temperature from the marine invertebrate Plexaura homomalla (Esper), 1972. Plexaura homomalla is a member of the subclass Octocorallia, order Goroacea, suborder Holazonia, family Plexauridae, genus plexaura. See, for example, Bayer, "The Shallow-Water Octocorallia of the West Indian Region", Martinus Nyhoff, The Hague (1961). A solution of PG ester in ethanol or benzene is contacted with a mixture of the esterase enzyme composition and water and is stirred until the ester is hydrolyzed, generally about 18–24 hours at 25° C. See for reference E. G. Daniels, Producing an Esterase, U.S. Pat. No. 3,761,356. Alternatively, direct saponification is used.

The final Formula VIII compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid additional salts, and quaternary ammonium salts. The choice of procedure depends in part upon the solubility characteristics of the particular salt to be prepared. In the case of the inorganic salts, it is usually suitable to dissolve the Formula VIII acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the Formula VIII acid is dissolved in a suitable solvent of either moderate or low polarity. Examples of the former are ethanol acetone, and ethyl acetate. Examples of the latter are diethyl ether and benzene. At least a stoichiometric amount of amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the Formula VIII acid with the stoichiometric amount of the corresponding quaternary ammonium hydroxide in water, solution, followed by evaporation of the water.

The final Formula VIII acids or esters prepared by the processes of this invention, wherein $R_6$ is hydrogen, are transformed to lower alkanoates by interaction of the Formula VIII hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 1000 moles of anhydride per mole of the hydroxy compound reactant. The excess anhydride serves as a reaction diluent and solvent. An inert organic diluent, for example, dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. the desired carboxyacylate is recovered from the diethyl ether extract by evaporation. The carboxyacylate is then purified by conventional methods, advantageously by chromatography.

By this procedure, the Formula VIII 11-deoxy PGE-type compounds are transformed to monoalkanoates.

DESCRIPTION OF THE PREFERRED EMBODIMENTS

The invention can be more fully understood by the following preparations and examples.

All temperatures are in degrees centigrade.

Infrared absorption spectra are recorded on a Perkin-Elmer model 421 infrared spectrophotometer. Except when specified otherwise, undiluted (neat) samples are used.

Mass spectra are recorded on an Atlas CH-4 mass spectrometer with a TO-4 source (ionization voltage 70 ev).

NMR spectra are recorded on a Varian A-60 spectrophotometer in deuterochloroform solutions with tetramethylsilane as an internal standard.

"Brine", herein, refers to an aqueous saturated sodium chloride solution.

Preparation 1: 4,4-Difluoro-4-carboxybutyltriphenyl phosphonium bromide, $Br(C_6H_5)_3P(CH_2)_3CF_2COOH$ 1. Methyl furoate (50.4 g.) dissolved in methanol (180 ml.) is hydrogenated in the presence of a 5% palladium on charcoal catalyst (1 g.) at a hydrogen pressure of 50 p.s.i. Following filtration, washing and distillation there is recovered methyltetrahydrofuroate (46.7 g.) boiling at 32–35° C. under 0.1 mm. Hg.

2. To 25 g. of methyl tetrahydrofuroate obtained in step 1, there is added a reagent obtained by bubbling anhydrous HBr through 50 ml. of acetic anhydride until a specific gravity of 1.3 is reached. This addition is made while excluding moisture and with cooling and stirring. The reaction is allowed to proceed overnight, then the reaction mixture is placed on crushed ice and water and then extracted with diethyl ether, the ether extract is washed with sodium hydroxide, dried over sodium sulfate, filtered and evaporated to yield an oil which is distilled to yield 31.6 g. of methyl-2-acetoxy-5-bromopentanoate, boiling at 93–99° C. under 0.2–0.3 mm. Hg 3. To a solution of 60 g. of the product of step 2 in 200 ml. of methanol, there is added 100 ml. of ice cold methanol saturated with HBr and the mixture is allowed to stand at room temperature overnight. After removal of the solvent, the residue is dissolved in ethyl acetate, washed with aqueous sodium hydroxide and then brine, dried over sodium sulfate, filtered, the solvent is evaporated, and the resultant oil is distilled to give 28.8 g. of methyl 2-hydroxy-5-bromo-pentanoate.

4. To a solution of 34.4 g. of the product of step 3 in 400 ml. of acetone, there is added with stirring 75 ml. of Jones reagent at a rate such that the reaction temperature is between 30° and 40° C. The reaction mixture is stirred for 1.5 hours after completing adding the reagent, then 150 ml. of isopropyl alcohol is added and stirring is continued for 30 mins. The reaction mixture is diluted with water and extracted with methylene chloride, the extract is washed with brine, dried over sodium sulfate, filtered and evaporated to obtain 30.8 g. of a pale yellow oil which is used in the next step without purification. Analysis of a sample of the oil showed that it comprised methyl 2-oxo-5-bromo-pentanoate.

5. A solution of 30.8 g. of the product of step 4 in methylene chloride (195 ml.) is added dropwise, with stirring, into 195 ml. of Fluoreze M(PCR Incorporated) under dry nitrogen atmosphere cooled in a dry ice/acetone bath to provide a reaction temperature of −35° to −45° C. After stirring for one hour, the cooling bath is removed and the mixture is diluted with methylene chloride and water, then extracted with methylene chloride. The extracts are washed with water, aqueous potassium hydrogen carbonate and brine, and then dried over sodium sulfate. After filtration and evaporation of the solvent, the brown oil is distilled to recover 14 g. of methyl 2,2-difluoro-5-bromo-pentanoate, boiling at 34°–48° C. at 0.1 mm. Hg.

6. Into 175 ml. of aqueous HBr there is added 28 g. of the product of step 5 and the reaction mixture is stirred at room temperature for three hours. The reaction mixture is cooled in an ice bath and diluted with diethyl ether. The aqueous layer is extracted with diethyl ether, the combined ether solutions are washed with water, dried over sodium sulfate, and the solvent is evaporated to yield 27.7 g. of pale yellow oil of 2,2-difluoro-5-bromo-pentanoic acid which is used in the next step without further purification.

7. Triphenylphosphine (156 g.) and 2,2-difluoro-5-bromo-pentanoic acid (120 g.) are heated in 125 ml. of benzene at reflux for 18 hours. The crystalline product is filtered off, washed with benzene and recrystallized from methanol-diethyl ether.

Preparation 2: 6-Carboxyhexyltriphenylphosphonium bromide, $Br(C_6H_5)_3P(CH_2)_6COOH$.

Triphenylphosphine (156 g.) and 7-bromoheptanoic acid (115 g.) are heated in 125 ml. of benzene at reflux for 18 hrs. The crystalline product is filtered off, washed with benzene, and recrystallized from methanol-diethyl ether, m.p. 185°-187° C.

Preparation 3:
2β-[(3S)-3-[(Tetrahydropyran-2-yl)oxy]trans-1-octenyl]-5α-hydroxy-1α-cyclopentaneacetaldehyde, γ-Lactol (Formula XIII:

and $R_7$ is n-butyl)

a. Refer to Chart A. The formula-IX starting material, 5α-hydroxy-2β-carboxaldehyde-1α-cyclopentaneacetic acid γ lactone is first prepared in optically active form. A solution of the racemic compound (E. J. Corey et al., Tetrahedron Lett. No. 49, 4753 (1971) 15.4 g.) and 1-ephedrine (16.5 g.) in 150 ml. of benzene is concentrated under reduced pressure to a residue. The residue is triturated with diethyl ether and then dissolved in isopropyl ether. The solution is chilled to yield crystals of one of the diastereomeric oxazolidines. The oxazolidine is hydrolyzed to the oxo compound and ephedrine by contract with water, preferably with an acid catalyst, as is known in the art (see Elderfeld Heterocyclic Compounds, Vol. 5, page 394, Wiley, N.Y. 1957). Thus, the above oxazolidine (1.3 g.) is stirred in a solution of tetrahydrofuran-water-acetic acid (25 ml.: 25 ml.: 5 ml.) for 4 hr. at about 25° C. under nitrogen. The solvents are removed under reduced pressure and the residue is mixed with 25 ml. of water. The mixture is extracted several times with benzene, and the combined benzene layers are washed with water, dried over sodium sulfate, and concentrated under reduced pressure to yield an optically active isomer of the formula-IX compound; called "the isomer of Preparation 3a" herein. Following the procedure of part a above, but replacing 1-ephedrine with d-ephedrine, there is obtained another diastereomeric oxazolidine which yields on hydrolysis an enantiomer of the isomer above, called "the isomer of Preparation 3a" herein.

b. Compound X is prepared as follows. There is first prepared a solution of the anion of dimethyl 2-oxoheptyl phosphonate (E. J. Corey et al., J. Am. Chem. Soc. 90, 3247 (1968)). The phosphonate (8.0 g.) is added in portions over a 2-3 min. period to a stirred mixture of sodium hydride (1.75 g. of 50%) in 250 ml. of dry tetrahydrofuran under nitrogen previously cooled to 5° C. Stirring is continued at about 25° C. for at least one hr. and the mixture is cooled to 0° C. There is then added a benzene solution of the formula IX aldehyde and stirring is continued for 1.5 hr. at about 25° C. Then about 3 ml. of acetic acid is added dropwise and the mixture is concentrated under reduced pressure. The residue is taken up in 400 ml. of ethyl acetate, washed with water and brine, dried over sodium sulfate, and concentrated under reduced pressure. The residue is dissolved in 50 ml. of dichloromethane and chromatographed on silica gel (500 g.) by elution gradient with 25-30% ethyl acetate in Skellysolve B. Those fractions shown by TLC to be free of starting material are combined and concentrated to an oil of the Formula X compound.

c. To a mixture of zinc borohydride prepared from zinc chloride (anhydrous, 19 g.) and sodium borohydride (4.3 g.) in 120 ml. of dry 1,2-dimethoxyethane under nitrogen stirred for 20 hr. and then cooled to −20° C., is added the Formula X ketone above (10.5 g.) in 55 ml. of 1,2-dimethoxyethane. The mixture is stirred at −20° C. for 17 hr., warmed to room temperature and stirred until reaction is complete as shown by TLC. The mixture is cooled to 0-5° C., and 30 ml. of water added dropwise. After hydrolysis is complete, the mixture is shaken with 200 ml. of ethyl acetate and separated. The ethyl acetate layer is washed with brine, dried over sodium sulfate, and concentrated under reduced pressure to give a mixture of the Formula XI isomers. The α and β isomers are separated by chromatography on a silica gel column by gradient elution with 35-60% ethyl acetate in Skellysolve B. Fractions containing the α or β isomers, as shown by TLC, are combined and concentrated to yield the desired hydroxy intermediates.

d. There is next prepared the Formula XII tetrahydropyranyl ether. The Formula XI alpha hydroxy compound above (10.0 g.) is treated with 20 ml. of dihydropyran in 120 ml. of dichloromethane in the presence of pyridine hydrochloride (0.12 g.). After about 2.5 hr. the mixture is filtered, washed with dilute aqueous potassium bicaronate, dried and concentrated to give the Formula XII compound wherein $M_2$ is

(See Corey et al., op. cit.).

e. To a solution of above lactone XII in 250 ml. of toluene at −78° C. is added dropwise, while stirring, diisobutylaluminum hydride (12.5 ml. in 60 ml. of toluene). Stirring is continued at −78° C. for one hr., whereupon a solution of 3 ml. of tetrahydrofuran and 1 ml. of water is added cautiously. After the mixture is stirred an additional 0.5 hr. at about 25° C., it is diluted with benzene and filtered. The filtrate is washed with brine, dried, and concentrated to the Formula XIII title compound. See Corey et al., op. cit.

Following the procedures of steps d, and e above, but employing the Formula XI beta hydroxy compound from step c, there are obtained the corresponding Formula XII and XIII compounds wherein $M_1$ is

and M₂ is

Likewise following the procedures of Preparation 3, but replacing the dimethyl 2-oxoheptylphosphonate of that preparation with the various phosphonates within the scope of

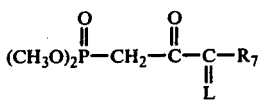

wherein L and R₇ are as defined above, there are obtained the corresponding Formula XIII compounds and their racemic compounds wherein M₂ is either

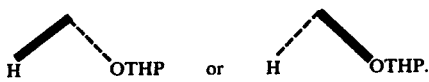

Those phosphonates are prepared by methods described herein or known in the art, utilizing for example the following aliphatic acid esters within the scope of

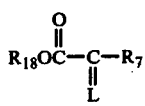

wherein L and R₇ are as defined above, and R₁₈ is methyl or ethyl:

methyl butyrate
methyl 2-fluorobutyrate
ethyl 2,2-difluorobutyrate
methyl valerate
methyl 2-methylvalerate
ethyl 2-fluorovalerate
methyl hexanoate
methyl-2,2-dimethyl hexanoate
ethyl 2-methylhexanoate
methyl 2-fluorohexanoate
methyl 2,2-difluorohexanoate
methyl heptanoate
methyl 2-methylheptanoate
methyl 2-fluoroheptanoate
methyl 2,2-difluoroheptanoate
ethyl octanoate
methyl 2-fluoroctanoate
methyl 2-methyloctanoate When the phosphonate contains an asymmetric carbon atom, e.g. when the methylene between the carbonyl and R₇ is substituted with only one methyl or fluoro group, the phosphonate exists in either of two optically active forms (+ or −) or their racemic (dl) mixture. An optically active phosphonate is obtained by starting with an appropriate optically active isomer of the aliphatic acid. Methods of resolving these acids are known in the art, for example by forming salts with an optically active base such as brucine, separating the resulting diastereomers, and recovering the acids.

Following the procedure of Preparation 3 employing the optically active aldehyde IX of that example, each optically active phosphonate obtained from the list of aliphatic acid esters above in the second paragraph following Preparation 3 yields a corresponding optically active Formula XIII γ-lactol.

Likewise following the procedure of Preparation 3, employing the optically active aldehyde IX of that example, each racemic phosphonate obtained from the above-mentioned list of aliphatic acid esters yields a pair of diastereomers, differing in their stereochemistry at the fourth carbon of the alkyl-termiated side-chain. These diastereomers are separated by conventional methods, e.g. by silica gel chromatography.

Again, following the procedure of Preparation 3, employing the optically active aldehyde IX of that example, each of the optically inactive phosphonates obtained from the list of aliphatic acid esters above wherein there is no asymmetric carbon atom, i.e. R₃ and R₄ are the same, yields a corresponding optically active Formula XIII γ-lactol.

Replacing the optically active aldehyde IX with the racemic aldehyde and following the procedure of Preparation 3 using each of the optically active phosphonates described above, there is obtained in each case a pair of diastereomers which are separated by chromatography.

Likewise following the procedure of Preparation 3, employing the racemic aldehyde with each of the racemic phosphonates described above, there are obtained in each case two pairs of 3-oxo racemates which are separated into pairs of racemic compounds by methods known in the art, e.g. silica gel chromatography.

Again following the procedure of Preparation 3, employing the racemic aldehyde with each of the optically inactive phosphonates described above, there are obtained in each case a racemic product corresponding to Formula XIII.

Preparation 4:
2β-[(3S)-5-Phenyl-3-[(tetrahydropyran-2-yl)-oxy]-trans-1-pentyl]-5α-hydroxy-1α-cyclopentaneacetaldehyde, γ-Lactol (Formula XIII: M₂ is

R₃ and R₄ are hydrogen, and R₇ is

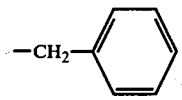

a. Refer to Chart A. The phosphonate anion(ylid) is first prepared as follows. Dimethyl 2-oxo-4-phenylbutylphosphonate (prepared by methods known in the art from dimethyl methylphosphonate and ethyl 3-phenylpropionate in the presence of butyllithium) (14.28 g.) is added to a suspension of sodium hydride (2.7 g.) in 250 ml. of tetrahydrofuran and stirring continued for 2 hr.

To the above suspension at 0° C. is added the Formula IX aldehyde (6.0 g.) in benzene. The mixture is stirred for 2 hr., acetic acid (1.5 ml.) is added, and the mixture is concentrated under reduced pressure. The residue is taken up in ethyl acetate, washed with brine, dried and concentrated. Silica gel chromatography yields the Formula X compound wherein R₇ and L are defined in the heading above.

b. To a mixture of zinc borohydride prepared from zinc chloride (anhydrous, 13.6 g.) and sodium borohydride (3.0 g.) in 120 ml. of 1,2-dimethoxyethane under nitrogen stirred for 2 hr. and then cooled to −10° C., is added the Formula X ketone above (8.1 g.) in 45 ml. of 1,2-dimethoxyethane. The mixture is stirred at 0° C. for 2 hr. and at about 25° C. for 1 hr. The mixture is cooled to 0°–5° C. and 19.5 ml. of water is added cautiously. After hydrolysis is complete, the mixture is shaken with 200 ml. of ethyl acetate and filtered. The filtrate is washed with brine, dried and concentrated under reduced pressure. The alpha and beta isomers are separated by silica gel chromatography, eluting with ethyl acetate-Skellysolve B (2:1). Fractions containing the α or β isomers as shown by TLC, are combined and concentrated to yield the Formula XI product where $M_1$ is

and the Formula XI product wherein $M_1$ is

c. There is next prepared the Formula XII tetrahydropyranyl ether wherein $M_2$ is

$R_3$ and $R_4$ are hydrogen, $R_7$ is

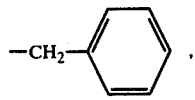

and $R_9$ is THP. The Formula XI compound above (1.985 g.) is treated with 4.95 ml. of dihydropyran in 45 ml. of dichloromethane in the presence of p-toluene-sulfonic acid (0.033 g.). After about 25 min. the mixture is washed with potassium bicarbonate solution, dried, and concentrated to give the Formula XII compound free of starting material by TLC.

d. To a solution of the above lactone in 45 ml. of toluene at −78° C. is added dropwise, while stirring, diisobutylaluminum hydride (3.9 ml.). Stirring is continued at −78° C. for 0.5 hr., whereupon a solution of 9 ml. of water in 17 ml. of tetrahydrofuran is added. After the mixture is stirred for an additional hour at about 25° C. it is filtered. The filtrate is washed with brine, dried, and concentrated to yield the Formula XIII title compound.

Following the procedures of steps c and d above, but employing the Formula XI β-hydroxy compound from step b, there are obtained the Formula XII and XIII compounds wherein $M_1$ is

and $M_2$ is

Following the procedures of Preparation 4, but replacing the Formula IX aldehyde with the racemic compound, there are obtained the racemic componds corresponding to Formula XIII.

Likewise, following the procedures of Preparation 4, but replacing the dimethyl 2-oxo-4-phenylbutylphosphonate of that preparation with the various phosphonates within the scope of

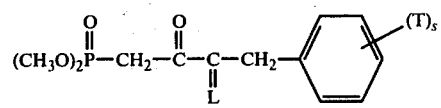

wherein T is alkyl of one to 3 carbon atoms, inclusive, fluoro, chloro, trifluoromethyl, or —$OR_8$, wherein $R_8$ is alkyl of one to 3 carbon atoms, inclusive, and s is zero, one, 2, or 3, with the proviso that when s is 2 or 3 the T's are either the same or different, wherein $R_3$ and $R_4$ are hydrogen, methyl or fluoro, being the same or different, with the proviso that $R_3$ is fluoro only when $R_4$ is hydrogen or fluoro, there are obtained the corresponding Formula XIII optically active γ-lactols and their racemic compounds wherein $M_2$ is either

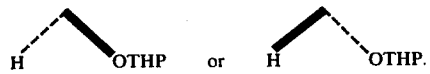

Those phosphonates are prepared by methods described herein or known in the art, utilizing the example the following aliphatic acid esters within the scope of

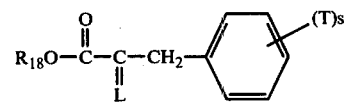

wherein $R_3$, $R_4$, s, and T are as defined above, and $R_{18}$ is methyl or ethyl, for example:

methyl 3-phenylpropionate
ethyl 3-(p-chlorophenyl)propionate
methyl 3-(o,p-dichlorophenyl)propionate
methyl 2-fluoro-3-(p-tolyl)propionate
methyl 3-(m-chlorophenyl)propionate
ethyl 3-(α,α,α-trifluoro-p-tolyl)propionate
ethyl 3-(α,α,α-trifluoro-m-tolyl)propionate
methyl 2,2-difluoro-3-phenylpropionate
methyl 3-(p-fluorophenyl)propionate
methyl 3-(m-fluorophenyl)propionate
ethyl-2-methyl-3-(p-chlorophenyl)propionate When the phosphonate contains an asymmetric carbon atom, e.g. when the methylene between the carbonyl and —$CH_2$— is substituted with only one methyl group, the phosphonate exists in either of two optically active forms (+ or −) or their racemic (dl) mixture. An optically active phosphonate is obtained by starting with an appropriate optically active isomer of the aliphatic acid. Methods of resolving these acids are known in the art, for example by forming salts with an optically active base such as brucine, separating the resulting diastereomers, and recovering the acids.

Following the procedure of Preparation 4, employing the optically active aldehyde IX of that example, each optically active phosphonate obtained from the list of aliphatic acid esters above in the third paragraph following Preparation 4 yields a corresponding optically active Formula XIII γ-lactol.

Likewise following the procedure of Preparation 4, employing the optically active aldehyde IX of that example, each racemic phosphonate obtained from the above-mentioned list of aliphatic acid esters yields a pair of diastereomers, differing in their stereochemistry at the fourth carbon of the phenoxy-terminated side-chain. These diastereomers are separated by conventional methods, e.g. by silica gel chromatography.

Again following the procedure of Preparation 4, employing the optically active aldehyde IX of that example, each of the optically inactive phosphonates obtained from the list of aliphatic acid esters above wherein there is no asymmetric carbon atom, i.e. $R_3$ and $R_4$ are the same, yields a corresponding optically active Formula XIII γ-lactol.

Replacing the optically active aldehyde IX with the racemic aldehyde, and following the procedure of Preparation 4 using each of the optically active phosphonates described above, there is obtained in each case a pair of diastereomers which are separated by chromatography.

Likewise following the procedure of Preparation 4, employing the racemic aldehyde with each of the racemic phosphonates described above, there are obtained in case two pairs of 3-oxo racemates which are separated into pairs of racemic compounds by methods known in the art, e.g. silica gel chromatography.

Again following the procedure of Preparation 4, employing the racemic aldehyde with each of the optically inactive phosphonates described above, there are obtained in each case a racemic product corresponding to Formula XIII.

Preparation 5:
2β-[(3S)-4-Phenoxy-3-[(tetrahydropyran-2-yl)-oxy]-trans-1-butyl]-5α-hydroxy-1α-cyclopentaneacetaldehyde, γ-Lactol (Formula XIII: $M_2$ is

$R_3$ and $R_4$ are hydrogen, and $R_7$ is

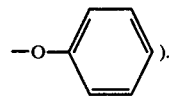

a. Refer to Chart A. There is first prepared dimethyl 3-phenoxyacetonylphosphonate. A solution of dimethyl methylphosphonate (75 g.) in 700 ml. of tetrahydrofuran is cooled to −75° C. under nitrogen and n-butyllithium (400 ml. of 1.6 molar solution of hexane) is added, keeping the temperature below −55° C. The mixture is stirred for 10 min. and to it is slowly added phenoxyacetyl chloride (44 g.), again keeping the temperature below −55° C. The reaction mixture is stirred at −75° C. for 2 hr., then at about 25° C. for 16 hr. The mixture is acidifed with acetic acid and concentrated under reduced pressure. The residue is partitioned between diethyl ether and water, and the organic phase is dried and concentrated to the above-named intermediate, 82 g. Further treatment by silica gel chromatography yields an analytical sample having NMR peaks at 7.4–6.7 (multiplet), 4.78 (singlet), 4.8 and 4.6 (two singlets), and 3.4–3.04 (doublet)δ.

b. The phosphonate anion (ylid) is then prepared as follows. Dimethyl 3-phenoxyacetonylphosphonate (step a, 9.3 g.) is added in portions to a cold (5° C.) mixture of sodium hydride (1.75 g.) 50%; in 250 ml of tetrahydrofuran, and the resulting mixture is stirred for 1.5 hr. at about 25° C.

c. To the mixture of step b is added the cold solution of the Formula IX aldehyde, and the resulting mixture is stirred about 1.6 hr. Then 3 ml. of acetic acid is added and the mixture is concentrated under reduced pressure. A solution is prepared from the residue in 500 ml. of ethyl acetate, washed with several portions of water and brine, and concentrated under reduced pressure. The residue is subjected to silica gel chromatography, eluting with ethyl acetate-Skellysolve B (isomeric hexanes) (3:1). Those fractions shown by TLC to be free of starting material and impurities are combined and concentrated to yield the Formula X compound.

d. Sodium borohydride (1.05 g.) is added in portions to a cold (0° C.) mixture of zinc chloride (4.4 g.) and 35 ml. of 1,2-dimethoxyethane under nitrogen. Stirring is continued at about 25° C. for 20 hr. Then the mixture is cooled to −20° C. and the Formula X 3-oxo compound (step c, 2.6 g. in 10 ml. of 1,2-dimethoxyethane is added. The mixture is stirred at −20° C. for 6 hr., and at 25° C. for 30min. The mixture is again cooled to −20° C. and 5 ml. of water is added dropwise. The mixture is shaken with 100 ml. of brine and ethyl acetate and the organic layer is dried and concentrated under reduced pressure. The residue is chromatographed on silica gel, eluting with ethyl acetate-Skellysolve B (isomeric hexanes) (3:1). Those fractions shown by TLC to be free of starting material and impurities are combined and concentrated to yield the 3α-hydroxy Formula XI compound. Other fractions yield the more polar 3β-hydroxy Formula XI compound.

e. The Formula XI compound from part d above is converted to the Formula XII tetrahydropyranyl ether by reaction with 0.8 ml. of dihydropyran in 10 ml. of dichloromethane in the presence of pyridine hydrochloride (about 0.03 g.). In about 2.5 hr. the mixture is filtered and concentrated to the Formula XII product.

f. The Formula XIII title compound is prepared as follows. Diisobutylaluminum hydride (4.8 ml. of a 10% solution in toluene) is added dropwise to a stirred solution of the Formula XII tetrahydropyranyl ether from step e above in 8 ml. of toluene cooled to −78° C. Stirring is continued at −78° C. for 0.5 hr., whereupon a solution of 3 ml. of tetrahydrofuran and 1 ml. of water is added cautiously. After the mixture warms to 25° C. it is filtered and the filtrate washed with brine, dried, and concentrated to the mixed alpha and beta hydroxy isomers of the Formula XIII title compounds.

Following the procedures of Preparation 5 steps e and f, but using the Formula XI 3β-hydroxy-4-phenoxy isomer of step d, there is obtained the corresponding 3β-hydroxy Formula XIII compound, i.e. wherein $M_2$ is

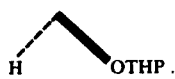

Following the procedure of Preparation 5, but replacing the optically active Formula IX aldehyde with the racemic aldehyde, there is obtained the racemic 3-hydroxy-4-phenoxy-1-butenyl compound corresponding to Formula XIII.

Following the procedure of Preparation 5, but replacing the phenoxyacetyl chloride in step a with each of the aliphatic acid esters or acid chlorides within the scope of

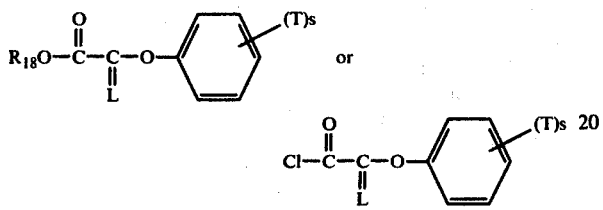

wherein $R_3$ and $R_4$ are hydrogen or methyl atoms, being the same or different, wherein $R_{18}$ is methyl or ethyl and wherein T is alkyl of one to 3 carbon atoms, inclusive, fluoro, chloro, trifluoromethyl, or $-OR_8$, wherein $R_8$ is hydrogen or alkyl of one to 3 carbon atoms, inclusive, and s is zero, one, 2 or 3, with the proviso that not more than two T's are other than alkyl and when s is 2 or 3 the T's are either the same or different, for example:

methyl phenoxyacetate
methyl p-fluorophenoxyacetate
methyl m-fluorophenoxyacetate
methyl 2-phenoxypropionate
methyl 2-methyl-2-phenoxypropionate
ethyl p-chlorophenoxyacetate
ethyl m-chlorophenoxyacetate
methyl (p-tolyloxy)acetate
methyl 2-(p-fluorophenoxy)propionate
ethyl (o,p-dichlorophenoxy)acetate
ethyl (α,α,α-trifluoro-p-tolyloxy)acetate
ethyl (α,α,α-trifluoro-m-tolyloxy-acetate
there are obtained the corresponding phosphonate and, thence, the Formula XIII γ-lactol.

Preparation 6:
2β-[(3S)-3-Methoxy-trans-1-octenyl]-5α-hydroxy-1α-cyclopentaneacetaldehyde, γ-Lactol (Formula XIX:

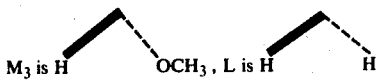

and $R_7$ is n-butyl)

Refer to Chart B. A mixture of the Formula XI alpha hydroxy compound wherein $M_1$ is

and $R_7$ is n-butyl (2.0 g.), silver oxide (4.0 g.) and 50 ml of methyl iodide is stirred and heated at reflux for 68 hr. The mixture is cooled and filtered, and the filtrate concentrated to a residue 2.0 g. The residue is subjected to silica gel chromatography to yield the Formula XVIII compound.

Thereafter following the procedures of Preparation 3 step e there is obtained the Formula XIX title compound γ-lactol.

Following the procedures of Preparation 6, but replacing the Formula XI alpha hydroxy compound wherein $R_7$ is n-butyl with corresponding Formula XI alpha hydroxy compounds wherein $R_7$ is as defined above for Formula VIII, prepared by using the alternative phosphonate reagents described in Preparations 3, 4 and 5, there are obtained the corresponding Formula XIX compounds.

Preparation 7:
2β-[(3S)-3-[(Tetrahydropyran-2-yl)oxy]-3-methyl-trans-1-octenyl]-5α-hydroxy-1α-cyclopentaneacetaldehyde, γ-Lactol (Formula XXIII:

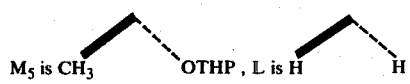

and $R_7$ is n-butyl).

Refer to Chart C. A solution of the Formula X oxo compound (Preparation 3-step b, 0.2 g.) in 15 ml of tetrahydrofuran is treated, with stirring at $-78°$ C., with 3M methyl magnesium bromide in ether, added dropwise. After 2 hr. there is added dropwise to the mixture at $-78°$ C. 10 ml of saturated aqueous ammonium chloride. The mixture is warmed to 25° C. and diluted with diethyl ether and water. The organic phase is washed with brine, dried and concentrated to the mixed 15R and 15S Formula XXI compounds.

Thereafter, following the procedures of Preparation 3 steps c-e and employing the alpha-hydroxy compound, there are obtained the Formula XXII compound and finally the Formula XXIII title compound.

Following the procedures of Preparation 7, but replacing the Formula X oxo compound wherein $R_7$ is n-butyl with corresponding Formula X oxo compounds wherein $R_7$ is as defined above for Formula VIII, prepared by using the alternative phosphonate reagents described in Preparations 3, 4 and 5, there are obtained the corresponding Formula XXIII compounds.

Preparation 8:
5α-Hydroxy-2β-[(3S)-3-hydroxy-trans-1-octenyl)]-1α-cyclopentanepropionaldehyde δ-Lactol (Formula XXV:

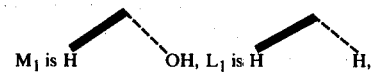

and $R_7$ is n-butyl).

1. Refer to Chart D. A suspension of methoxymethyltriphenylphosphonium chloride (Levine, J. Am. Chem. Soc. 80, 6150 (1958), 32.4 g.) in 150 ml of tetrahydrofuran (THF) is cooled to $-15°$ C and to it is added 69.4 ml of butyllithium (1.6 M in hexane) in 45 ml of THF. After 30 min. there is added a solution of the Formula XIII compound (Preparation 3, 10.0 g.) in 90 ml of THF. The mixture is stirred for 1.5 hrs., meanwhile warming to about 25° C., and is then concentrated under reduced pressure. The residue is partitioned between dichloromethane and water, and the organic phase is dried and concentrated. This residue is then subjected to chromatography over silica gel, eluting with cyclohexane-ethyl acetate (2:1). Those fractions shown by thin-layer chromatography (TLC) to contain the Formula XXIV intermediate are combined and concentrated to yield that enol-ether, 5.2 g.

2. The above enol-ether, in 20 ml of THF, is hydrolyzed with 50 ml of 66% acetic acid at about 57° C. for 2.5 hrs. The mixture is concentrated under reduced pressure. Toluene is added to the residue and the solution is again concentrated. Finally the residue is subjected to chromatography on silica gel, eluting with chloroform-methanol (6:1). The title compound is obtained by combining and concentrating suitable fractions, 2.54 g.: recrystallized from ethyl acetate.

Following the procedures of Preparation 8, but replacing the Formula XIII compound with the corresponding 3β-hydroxy ether compound there is obtained the corresponding Formula XXV 3β-hydroxy compound. Likewise, the racemic 3α- or 3β-hydroxy ether compounds yield the corresponding racemic 3α or 3β-hydroxy δ-lactols.

Preparation 9:
5α-Hydroxy-2β-[(3S)-3-methoxy-trans-1-octenyl]-1α-cyclopentanepropionaldehyde δ lactol (Formula XXXVII:

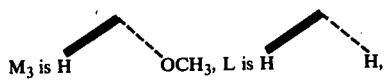

M₃ is H      OCH₃, L is H      H, and R₇ is n-butyl)

Refer to Chart F. Following the procedures of Preparation 8, but replacing the Formula XIII compounds with the corresponding Formula XIX compounds, there is obtained the corresponding Formula XXXVIII compounds.

Preparation 10:
5α-Hydroxy-2β-[(3S)-3-hydroxy-trans-1-octenyl] cyclopentane-1α-propionic acid, γ-lactone (Formula XXXI:

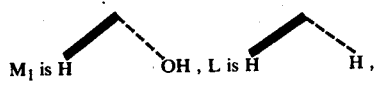

M₁ is H      OH, L is H      H, and R₇ is n-butyl)

Refer to Chart E. Silver oxide reagent is prepared by the addition of 145 ml of 2N NaOH to a stirred solution of silver nitrate (24.3 g.) in 61 ml of water. To this mixture is added the Formula XXV lactol (17.4 g.) in 110 ml of tetrahydrofuran. After 65 hr. a second slurry of silver oxide reagent is added. After 24 hr. the mixture is filtered, washed with water and diethyl ether. The aqueous extract is acidified to pH 1-2 with 2M NaHSO₄, extracted with diethyl ether, the extracts are combined, washed with water and brine, dried over sodium sulfate and azeotroped with benzene to recover crude Formula XXX acid (14.9 g.).

The crude acid is dissolved in methylene chloride, 3 g. of pyridine HCl is added and the resulting solution is stirred at room temperature under nitrogen. After 23 hr., the solvent is removed by evaporation at 40° C., the residue is dissolved in methylene chloride, filtered through silica gel with washing with ethyl acetate and 75% acetone-methylene chloride. The filtrate is evaporated to yield a crude product which is chromatographed on silica gel packed in 20% acetone-methylene chloride. Those fractions shown by TLC to be free of starting material are combined to give 6.1 g. of the title compound.

Example 1: 11-Deoxy-2,2-difluoro-PGE₂(Formula XVI: R₂ is fluoro, "m" is one, M₁ is

R₃ and R₄ are hydrogen and R₇ is n-butyl).

a. A mixture of 57% sodium hydride in mineral oil (0.84 g.) and dimethylsulfoxide is stirred under nitrogen at 60-65° C. for 1.5 hours and then cooled to 25° C. 4,4-Difluoro-4 carboxybutyltriphenylphosphonium bromide (Preparation 1, 4.43 g.) is added and the mixture is stirred at 36-40° C for 15 minutes. The Formula XIII lactol (Preparation 3) dissolved in dimethylsulfoxide (20 ml) is added dropwise during 5 min. and is stirred for 16 hours. Benzene (50 ml) is added and the mixture is cooled in an ice bath and a solution of potassium bisulfate (3.54 g.) in water (40 ml) is added. The mixture is diluted with water (200 ml), extracted with benzene, the extracts washed with water, dried and concentrated to yield 3.7 g. of yellow oil. The oil is slurried with diethyl ether, filtered and concentrated to yield 1.50 g. of yellow oil. The oil is chromatographed on acid washed silica gel eluted with 30% ethyl acetate - Skellysolve B. There is obtained the Formula XIV compound.

b. A stirred solution of the Formula XIV compound in acetone (15 ml) is cooled to −20° C. and there is added the Jones reagent (1 ml). The mixture is stirred at −20° C. for 38 minutes, then 1 ml of isopropanol is added and the mixture is stirred at −20° C. for an additional 10 minutes. The mixture is diluted with water and extracted with diethyl ether. The extracts are washed with brine, dried and concentrated to yield an oil of the Formula XV compound.

c. A mixture of the oil from step b., tetrahydrofuran (5 ml), water (5 ml) and acetic acid (10 ml) is heated at 42° C. for 3.5 hours. After adding water (20 ml) the mixture is frozen and freeze dried. The oil obtained is chromatographed on acid washed silica gel (20 g.), eluting with 40% ethyl acetate - Skellysolve B to yield 120 mg. of the title compound.

Following the procedure of Example 1, but replacing the Formula XIII compound of that Example with the corresponding Formula XIII compounds identified in and following Preparations 3, 4 and 5, there are obtained the corresponding Formula XVI compounds, including their methyl esters, for example:

11-deoxy-2,2-difluoro-PGE₂, methyl ester
11-deoxy-2,2-difluoro-16,16-dimethyl-PGE₂, and its methyl ester
11-deoxy-2,2,16,16-tetrafluoro-PGE₂, and its methyl ester
11-deoxy-2,2-difluoro-17-phenyl-18,19,20-trinor-PGE₂, and its methyl ester
11-deoxy-2,2-difluoro-17-(p-fluorophenyl)-18,19,20-trinor-PGE₂, and its methyl ester
11-deoxy-2,2-difluoro-17-(m-trifluoromethyl)phenyl-18,19,20-trinor-PGE₂, and its methyl ester 11-deoxy-2,2-difluoro-16-phenoxy-17,18,19,20-tetranor-PGE$_2$, and its methyl ester 11-deoxy-2,2-difluoro-16-(p-fluorophenoxy)-17,18,19,20-tetranor-PGE$_2$, and its methyl ester 11-deoxy-2,2-difluoro-16-(m-trifluoromethyl)phenoxy-17,18,19,20-tetranor-PGE$_2$, and its methyl ester Following the procedure of Example 1, but replacing the 4,4-difluoro-4-carboxybutyltriphenylphosphonium bromide with 4-carboxybutyltriphenylphosphonium bromide, 5,5-difluoro-5-carboxypentyltriphenylphosphonium bromide, 5-carboxypentyltriphenylphosphonium bromide, 6,6-difluoro-6-carboxyhexylphosphonium bromide or 6-carboxyhexylphosphonium bromide, and replacing the Formula XIII compound of that Example with the corresponding Formula XIII compounds of Preparations 3,4 and 5, yields the corresponding Formula XVI compounds, including their methyl esters, for example:

11-deoxy-16,16-difluoro-PGE$_2$, and its methyl ester
11-deoxy-16-fluoro-PGE, and its methyl ester
11-deoxy-16,16-difluoro-17-phenyl-18,19,20-trinor-PGE$_2$, and its methyl ester
11-deoxy-16,16-difluoro-17-(p-fluorophenyl)-18,19,20-trinor-PGE$_2$, and its methyl ester
11-deoxy-16,16-difluoro-17-(m-trifluoromethyl)phenyl-18,19,20-trinor-PGE$_2$, and its methyl ester
11-deoxy-16-phenoxy-17,18,19,20-tetranor-PGE$_2$, and its methyl ester
11-deoxy-16-methyl-16-phenoxy-17,18,19,20-tetranor-PGE$_2$, and its methyl ester
11-deoxy-16-(p-fluorophenoxy)-17,18,19,20-tetranor-PGE$_2$, and its methyl ester
11-deoxy-16-(m-trifluoromethyl)phenoxy-17,18,19,20-tetranor-PGE$_2$, and its methyl ester Example 2: 11-Deoxy-2,2-difluoro-PGF$_{2\alpha}$(Formula XVII: R$_2$ is fluoro, "m" is one, M$_1$ is

R$_3$ and R$_4$ are hydrogen and R$_7$ is n-butyl)

The title compound is obtained by hydrolyzing the Formula XIV tetrahydropyranyl ether (Example 1, part a, 0.8 g.) in a mixture of 5.6 ml. of THF and 18.6 ml. of 67% (aqueous) acetic acid. The mixture is warmed to about 40°-50° C. for 2 hrs., then concentrated under 1 mm. pressure. The residue is dissolved in benzene and chromatographed over silica gel using chloroform-methanol (4:1) for elution. Those fractions shown by TLC to contain the desired product are combined and concentrated to yield the Formula XVII title compound.

Following the procedures of Example 2, the other Formula XIV compounds prepared as described in the first and second paragraphs following Example 1 are transformed to the corresponding Formula XVII compounds.

Example 3: 11-Deoxy-15-methyl ether-PG-type compounds (Formula VIII: M is

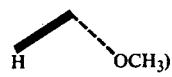

Refer to Chart B. Following the procedure of Examples 1 and 2, but replacing the Formula XIII lactol of Example 1 with the Formula XIX lactol, there is obtained the corresponding 11-deoxy-15-methyl ether type compound.

Following the procedures of Examples 1 and 2, but replacing the Preparation-3α-lactol with each of the appropriate Formula XIX lactols prepared by transforming each of the Formula XI lactols identified in and following Preparations 3, 4 and 5, to the corresponding methyl ether-type lactols of Formula XIX, there are obtained the corresponding 11-deoxy-15-methyl ether-type compounds, and their methyl esters, for example:

11-deoxy-2,2-difluoro-15-methyl ether-PGE$_2$, and its methyl ester
11-deoxy-2,2-difluoro-15-methyl ether-17-phenyl-18,19,20-trinor-PGE$_2$, and its methyl ester
11-deoxy-2,2-difluoro-15-methyl ether-17-(p-fluorophenyl)-18,19,20-trinor-PGE$_2$, and its methyl ester
11-deoxy-2,2-difluoro-15-methyl ether-17-(m-trifluoromethyl)phenyl-18,19,20-trinor-PGE$_2$, and its methyl ester
11-deoxy-2,2-difluoro-15-methyl ether-16-phenoxy-17,18,19,20-tetranor-PGE$_2$, and its methyl ester
11-deoxy-2,2-difluoro-15-methyl ether-16-(p-fluorophenoxy)-17,18,19,20-tetranor-PGE$_2$, and its methyl ester
11-deoxy-2,2-difluoro-15-methyl ether-16-(m-trifluoromethyl)phenoxy-17,18,19,20-tetranor-PGE$_2$, and its methyl ester
11-deoxy-15-methyl ether-16-phenoxy-17,18,19,20-tetranor-PGE$_2$, and its methyl ester
11-deoxy-15-methyl ether-16-(p-fluorophenoxy)-17,18,19,20-tetranor-PGE$_2$, and its methyl ester
11-deoxy-15-methyl ether-16-(m-trifluoromethyl)phenoxy-17,18,19,20-tetranor-PGE$_2$, and its methyl ester Example 4: 11-Deoxy-15-methyl-type compounds (Formula VIII: M is

and the corresponding 15-epi-isomer M is

Following the procedures of Example 1, but replacing the Formula XIII compound of Example 1 with the mixed 15-α and 15-β Formula XXIII compounds obtained above, there are obtained 11-deoxy-(15α and 15β)-15-methyl-PGE$_2$-type compounds, and their methyl esters, for example:

11-deoxy-2,2-difluoro-15-methyl-PGE$_2$, and its methyl ester 11-deoxy-2,2-difluoro-15-methyl-17-phenyl-18,19,20-trinor-PGE$_2$, and its methyl ester 11-deoxy-2,2-difluoro-15-methyl-17-(p-fluorophenyl)-18,19,20-trinor-PGE$_2$, and its methyl ester 11-deoxy-2,2-difluoro-15-methyl-17-(m-trifluoromethyl)-phenyl-18,19,20-trinor-PGE$_2$, and its methyl ester 11-deoxy-2,2-difluoro-15-methyl-16-phenoxy-17,18,19,20-tetranor-PGE$_2$, and its methyl ester 11-deoxy-2,2-difluoro-15-methyl-16-(p-fluorophenoxy)-17,18,19,20-tetranor-PGE$_2$, and its methyl ester 11-deoxy-2,2-difluoro-15-methyl-16-(m-trifluoromethyl)phenoxy-17,18,19,20-tetranor-PGE$_2$, and its methyl ester 11-deoxy-15-methyl-16-phenoxy-17,18,19,20-tetranor-PGE$_2$, and its methyl ester 11-deoxy-15-methyl-16-(p-fluorophenoxy)-17,18,19,20-tetranor-PGE$_2$, and its methyl ester 11-deoxy-15-methyl-16-(m-trifluoromethyl)phenoxy-17,18,19,20-tetranor-PGE$_2$, and its methyl ester Example 5: 11-Deoxy-4,5,-cis-didehydro-PGF$_{1\alpha}$ (Formula XXVI:

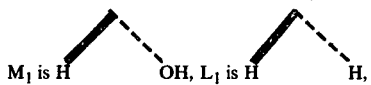

and R$_7$ is n-butyl).

Refer to Chart D. 3-Carboxypropyltriphenylphosphonium bromide is prepared by heating triphenylphosphine (156.8 g.) and 4-bromobutyric acid (100 g.) in 125 ml. of benzene at reflux for 18 hrs. The crystalline product is filtered off, washed with benzene, and recrystallized from ethanol-acetonitrile-ether, 150 g., m.p. 247°-249° C.

The above phosphonium bromide (10.6 g.) is added to sodio methylsulfinylcarbanide prepared from sodium hydride (2.08 g., 57%) and 30 ml. of dimethyl sulfoxide, and the resulting Wittig reagent is combined with the Formula XXV lactol of Preparation 8, in 20 ml. of dimethyl sulfoxide. The mixture is stirred overnight, diluted with about 200 ml. of benzene, and washed with potassium hydrogen sulfate solution. The two lower layers are washed with dichloromethane, and the organic phases are combined, washed with brine, dried, and concentrated under reduced pressure. The residue is subjected to chromatography over acid-washed silica gel, eluting with ethyl acetate-isomeric hexanes (3:1). Those fractions shown to contain the desired compound by TLC are combined and concentrated to yield the title compound.

Following the procedures of Example 5, but replacing the Formula XXV lactol of that Example with the corresponding Formula XXV 3β-hydroxy compound obtained following Preparation 8, there is obtained the corresponding Formula XXVI 11-deoxy-4,5-cis-didehydro-15β-PGF$_{1\alpha}$ product.

Following the procedures of Example 5, but replacing the Formula XXV lactol with the corresponding racemic 3α- or 3β-hydroxy lactol obtained following Preparation 8, there is obtained the corresponding dl-11-deoxy-4,5-cis-didehydro-PGF$_{1\alpha}$ or dl-11-deoxy-4,5-cis-didehydro-15β-PGF$_{1\alpha}$ product.

Likewise following the procedures of Example 5, but replacing the Formula XXV lactol with the various optically active or racemic 3α- or 3β-hydroxy lactols obtained following Preparations 3, 4 and 5, for example, wherein R$_7$ is within the scope defined for Formula VIII there is obtained the corresponding optically active or racemic 11-deoxy-4,5-cis-didehydro-PGF$_{1\alpha}$ or 11-deoxy-4,5-cis-didehydro-15β-PGF$_{1\alpha}$ type product.

Example 6: 11-Deoxy-4,5-cis-didehydro-PGF$_{1\alpha}$, Methyl Ester (Formula VIII: R$_1$ is methyl, R$_2$ is hydrogen, m is one, x is —CH$_2$—CH=CH—,

and R$_7$ is n-butyl).

A solution of diazomethane (about 50% excess) in diethyl ether (25 ml.) is added to a solution of 11-deoxy-4,5-cis-didehydro-PGF$_{1\alpha}$ (Example 5, 50 mg.) in 25 ml. of a mixture of methanol and diethyl ether (1:1). The mixture is left standing at 25° C. for 5 min. and then is concentrated under reduced pressure to the title compound.

Following the procedure of Example 6, each of the 11-deoxy-4,5-cis-didehydro-PGF$_{1\alpha}$ type products obtained following Example 5, including their 15-epimers and the racemic forms, is transformed to a corresponding methyl ester.

Example 7: 11-Deoxy-4,5-cis-didehydro-PGE$_1$, Methyl Ester (Formula VIII: R$_1$ is methyl, R is hydrogen, m is one, x is —CH$_2$—CH=CH—,

and R$_7$ is n-butyl).

Refer to Chart D. 1. A solution of 11 deoxy-4,5-cis-didehydro-PGF$_{1\alpha}$, methyl ester (Example 6, 480 mg.) in 20 ml. of acetone is cooled to about -50° C. and to it is added 4 ml. of N-trimethylsilyldiethylamine. The mixture is kept under nitrogen at −50° C. for 2.5 hrs. Progress of the reaction is monitored by TLC. The reaction mixture is diluted with about 200 ml. of diethyl ether. The solution is washed with about 150 ml. of cold brine and cold saturated potassium bicarbonate solutions. The ether extract is concentrated to a residue containing 11-deoxy-4,5-cis-didehydro-PGF$_{1\alpha}$, 15-trimethylsilyl ether, methyl ester (Formula XXVII).

2. For the oxidation step, a solution of the above 15-trimethylsilyl ether in dichloromethane (4 ml.) is added to a solution of CrO$_3$-pyridine (prepared from 0.26 g. of CrO$_3$ and 0.4 ml. of pyridine in 16 ml. of dichloromethane). The mixture is stirred for 5 min. at about 0° C. and 5 min. at about 25° C., then diluted with 10 ml. of ethyl acetate and filtered through silica gel. The solution, together with rinsings, is concentrated under reduced pressure to yield the Formula XXVIII compound.

3. The product of step 2 is hydrolyzed in 6 ml. of methanol, 1 ml. of water, and about 0.1 ml. of acetic acid at about 35° C. for 15 min. The volatiles are removed under reduced pressure and the residue is partitioned between dichlormethane and water. The organic phase is separated, dried over sodium sulfate, and concentrated under reduced pressure. The residue is chromatographed on silica gel, eluting with ethyl acetate- Skellysolve B (isomeric hexanes) (4:1). Those fractions containing the title compound free of starting material and impurities are combined and concentrated to yield the title compound.

Following the procedures of Example 7, but replacing 11-deoxy-4,5-cis-didehydro-PGF$_{1\alpha}$, methyl ester, with 11-deoxy-4,5-cis-didehydro-15$\beta$-PGF$_{1\alpha}$ obtained following Example 5, there is obtained the 11-deoxy-4,5-cis-didehydro-15$\beta$-PGE$_1$ product. Similarly, the corresponding racemic PGF$_{1\alpha}$ type compounds yield the corresponding racemic PGE$_1$ type products.

Likewise following the procedures of Example 7, but employing the various optically active or racemic PGF$_{1\alpha}$ or 15$\beta$-PGF$_{1\alpha}$ type compounds, or their methyl esters, there are obtained the corresponding optically active or racemic 11-deoxy-4,5-cis-didehydro-PGE$_1$ or 11-deoxy-4,5-cis-didehydro-15$\beta$-PGE$_1$ type products, for example:

11-deoxy-4,5-cis-didehydro-16,16-difluoro-PGE$_1$, and its methyl ester 11-deoxy-4,5-cis-didehydro-2,2,16,16-tetrafluoro-PGE$_1$, and its methyl ester 11-deoxy-4,5-cis-didehydro-17-phenyl-18,19,20-trinor-PGE$_1$, and its methyl ester 11-deoxy-4,5-cis-didehydro-17-(p-fluorophenyl)-18,19,20-trinor-PGE$_1$, and its methyl ester 11-deoxy-4,5-cis-didehydro-17-(m-trifluoromethyl)phenyl-18,19,20-trinor-PGE$_1$, and its methyl ester 11-deoxy-4,5-cis-didehydro-16-phenoxy-17,18,19,20-tetranor-PGE$_1$, and its methyl ester 11-deoxy-4,5-cis-didehydro-16-(p-fluorophenoxy)-17,18,19,20-tetranor-PGE$_1$, and its methyl ester 11-deoxy-4,5-cis-didehydro-16-(m-trifluoromethyl)phenoxy-17,18,19,20-tetranor-PGE$_1$, and its methyl ester 11-deoxy-4,5-cis-didehydro-2,2-difluoro-PGE$_1$, and its methyl ester 11-deoxy-4,5-cis-didehydro-2,2-difluoro-17-phenyl-18,19,20-trinor-PGE$_1$, and its methyl ester 11-deoxy-4,5-cis-didehydro-2,2-difluoro-17-(p-fluorophenyl)-18,19,20-trinor-PGE$_1$, and its methyl ester 11-deoxy-4,5-didehydro-2,2-difluoro-17-(m-trifluoromethyl)phenyl-18,19,20-trinor-PGE$_1$, and its methyl ester 11-deoxy-4,5-cis-didehydro-2,2-difluoro-16-phenoxy-17,18,19,20-tetranor-PGE$_1$, and its methyl ester 11-deoxy-4,5-cis-didehydro-2,2-difluoro-16-(p-fluorophenoxy)-17,18,19,20-tetranor-PGE$_1$, and its methyl ester 11-deoxy-4,5-cis-didehydro-2,2-difluofo-16-(m-trifluoromethyl)phenoxy-17,18,19,20-tetranor-PGE$_1$, and its methyl ester Example 8: 11-Deoxy-4,5-cis-didehydro-PGF$_{1\alpha}$ and —PGE$_1$-type compounds Refer to Chart E. Following the procedures of Examples 1 and 2, but replacing the Formula XI lactone with the Formula XXXI lactone (Preparation 10), there are obtained the corresponding 11-deoxy-4,5-cis-didehydro compounds.

Example 9: 11-Deoxy-4,5-cis-didehydro-15-methyl ether-PGF$_{1\alpha}$ and -PGE$_1$-type compounds Refer to Chart F. Following the procedure of Example 5, but replacing the formula XIII lactol with the Formula XIX lactol (Preparation 6), there are obtained the corresponding 11-deoxy-4,5-cis-didehydro-15-methyl ether-PGF$_{1\alpha}$ compounds are transformed to the corresponding PGE$_1$ compoumds by the procedure of step 2 of Example 7.

Example 10:
11-Deoxy-4,5-cis-didehydro-15-methyl-PGF$_{1\alpha}$, Methyl Ester (Formulas XLII and XLII: R$_1$ is methyl, R$_2$ is hydrogen, m is one, L is

and R$_7$ is n-butyl)

1. Refer to Chart G. A solution of 11-deoxy-4,5-cis-didehydro-PGF$_{1\alpha}$ methyl ester (Example 6, about 0.5 g.) in 24 ml of dioxane is stirred at 50° under nitrogen and 2,3-dichloro-5,6-dicyano-1,4-benzoquinone (0.37 g.) is added. The mixture is stirred at 50° C. for 24 hrs., cooled to room temperature, and filtered. The filter cake is washed with tetrahydrofuran, and the filtrate and wash are combined and concentrated under reduced pressure. The residue is taken up in dichloromethane and washed with brine, then dried over sodium sulfate and concentrated under reduced pressure. The residue is chromatographed on silica gel, eluting with 2-10% ethanol in dichloromethane. Fractions shown by TLC to contain the desired product are combined and concentrated to give the Formula XL 15-oxo intermediate. 2. A solution of about 0.4 g. of the above 15-oxo compound, hexamethyldisilazane (3 mil) and trimethylchlorosilane (0.5 ml) in 20 ml of tetrahydrofuran is allowed to stand at about 25° C. for 20 hours. The mixture is filtered and the filtrate is concentrated by evaporation under reduced pressure. Xylene (10 ml) is added to the residue and removed by evaporation under reduced pressure.

3. The residue of step 2 is dissolved in anhydrous ether and 110% of the theoretical amount of 3 M methyl magnesium bromide in ether is added. The mixture is allowed to stand 20 min. at about 25° C. and poured into 100 ml of saturated aqueous ammonium chloride. The ether layer is separated, the aqueous layer is extracted with ether, and the ether extracts are combined and washed with brine, dried over sodium sulfate, and evaporated under reduced pressure. The residue is dissolved in 300 ml of ethanol and 30 ml of water containing 3 drops of glacial acetic acid, and the mixture is stirred for 2 hrs. at about 25° C. The mixture is concentrated under reduced pressure to an aqueous residue and the residue is extracted with dichloromethane. The dichloromethane extract is evaporated under reduced pressure to give a residue which is chromatographed over silica gel, eluting with 5%–10% ethanol in dichloromethane. Fractions shown by TLC to contain the desired product are combined and concentrated to yield the desired Formula XLII compound. Other fractions yield the 15-epimer corresponding to Formula XLIII.

Example 11:
11-Deoxy-4,5-cis-didehydro-15-methyl-PGE$_1$-type compounds (Formula XLVI: R$_2$ is hydrogen, m is one, L is

and R7 is n-butyl)

Refer to Chart H. Following the procedure of Example 7, the 11-deoxy-4,5-cis-didehydro-15-methyl-PGF$_{1\alpha}$-type compounds of Example 10 are transformed to the corresponding PGE$_1$-type compounds.

Example 12: 11-Deoxy-PGF-type compounds (Formula XLVIII)

Refer to Chart I. The Formula XLVII 11-deoxy-2,2-difluoro-PGE$_2$ (Example 1, 0.2 g.) is treated in 6 ml of methanol at 0° C., while stirring, with a solution of 50 mg of sodium borohydride in 0.5 ml of water. The mixture is stirred at 0° C. for 10 min. and then diluted with 100 ml of ethyl acetate. The organic phase is washed with brine, dried, and concentrated under reduced pressure. The residue is subjected to silica gel chromatography eluting with 5-20% ethanon in chloroform. The first 200 ml of eluant are discarded and then 10 ml fractions are collected yielding 11-deoxy-2,2-difluoro-PGF$_{2\alpha}$. Other fractions yield 11-deoxy-2,2-difluoro-PGF$_{2\beta}$.

Example 13: 11-Deoxy-13,14-dihydro-PG-type compounds

1. Refer to Chart J. A solution of Formula XI lactone prepared by steps a-c of Preparation 3 (100 mg) in 10 ml of ethyl acetate is shaken with hydrogen at about one atmospheric pressure at 25° C. in the presence of 5% palladium-on-carbon (15 mg). After approximately one equivalent of hydrogen is absorbed in about one hour, the hydrogenation is stopped, and the catalyst is removed by filtration. The filtrate is evaporated, and the residue is chromatographed on silica gel, eluting with 50-100% ethyl acetate gradient in Skellysolve B. Those fractions shown by TLC to contain the desired Formula XLIX product free of the starting product and impurities are recovered.

Following the procedures of steps d and e of Preparation 3 and Example 1, but replacing the Formula XI lactol of Preparation 3 with the lactol of step 1 above, there is obtained 11-deoxy-2,2-difluoro-13,14-dihydro-PGE$_1$.

Following the procedures of Example 13, but replacing the Formula XI lactone with the corresponding Formula XXI, Formila XXV and Formula XXXVII compounds, there are obtained the corresponding Formula L, Formula LI and Formula LII compounds which can be transformed to 11-deoxy-13,14-dihydro type compounds by the procedures of the preceding Examples.

Example 14: 11-Deoxy-13,14-dihydro-PG$_1$-type compounds (Formula LIV)

Refer to Chart K. A suspension of disodium azodiformate (50 mg.) in 5 ml. of absolute ethenol is added to a stirred solution of 11-deoxy-2,2-difluoro-PGE$_2$ (Example 1, 50 mg.) in 10 ml. of absolute ethanol under nitrogen at 25° C. The mixture is made acid with glacial acetic acid, and then is stirred under nitrogen at 25° C. for 8 hr. The resulting mixture is concentrated under reduced pressure, and the residue is mixed with a mixture of diethyl ether and water (1:1). The diethyl ether layer is separated, dried and concentrated to give 11-deoxy-2,2-difluoro-13,14-dihydro-PGE$_1$.

We claim:

1. A compound of the formula

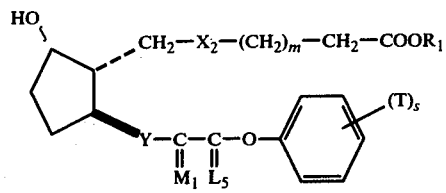

wherein Y is —CH$_2$CH$_2$— or trans—CH=CH—;
wherein m is one to 3, inclusive;
wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro, or alkyl of one to 3 carbon atoms, inclusive or a pharmacologically acceptable cation;
wherein L$_5$ is

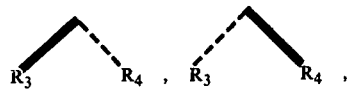

or a mixture of

wherein R$_3$ and R$_4$ are hydrogen or methyl, being the same or different;
wherein M$_1$ is

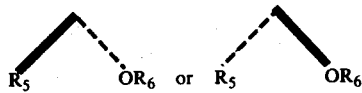

wherein R$_5$ and R$_6$ are hydrogen or methyl, with the proviso that R$_5$ is methyl only when R$_6$ is hydrogen, and R$_6$ is methyl only when R$_5$ is hydrogen;
wherein X$_2$ is —(CH$_2$)$_3$— or cis-CH=CH—CH$_2$—; and
wherein T is alkyl of one to 3 carbon atoms, inclusive, chloro, fluoro, trifluoromethyl, or —OR$_8$, wherein R$_8$ is alkyl of one to 3 carbon atoms, inclusive, and s is zero to 3, inclusive, the various T's being the same or different.

2. A compound according to claim 1, wherein s is zero or one and T is chloro, fluoro, or trifuloromethyl.

3. A compound according to claim 2, wherein R$_1$ is hydrogen, alkyl of one to 2 carbon atoms, inclusive or a pharmacologically acceptable cation.

4. 11-Deoxy-16-phenoxy-17,18,19,20-tetranor-PGF$_{2\alpha}$, methyl ester, a compound according to claim 3.

* * * * *